(12) United States Patent
Tseng et al.

(10) Patent No.: US 11,154,600 B2
(45) Date of Patent: *Oct. 26, 2021

(54) USE OF ANTI-CD47 AGENTS TO ENHANCE IMMUNIZATION

(71) Applicant: The Board of Trustees of the Leland Stanford Junior University, Stanford, CA (US)

(72) Inventors: Diane Tseng, San Jose, CA (US); Jens-Peter Volkmer, Menlo Park, CA (US); Kipp Andrew Weiskopf, Brookline, MA (US); Stephen Willingham, Sunnyvale, CA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 691 days.

This patent is subject to a terminal disclaimer.

(21) Appl. No.: 16/048,862

(22) Filed: Jul. 30, 2018

(65) Prior Publication Data
US 2018/0353582 A1    Dec. 13, 2018

Related U.S. Application Data

(63) Continuation of application No. 14/786,898, filed as application No. PCT/US2014/035167 on Apr. 23, 2014, now Pat. No. 10,064,925.

(60) Provisional application No. 61/817,229, filed on Apr. 29, 2013.

(51) Int. Cl.
| A61K 39/395 | (2006.01) |
| A61K 39/00 | (2006.01) |
| C12N 5/0786 | (2010.01) |

(52) U.S. Cl.
CPC .... *A61K 39/001129* (2018.08); *C12N 5/0645* (2013.01); *A61K 2039/5154* (2013.01); *A61K 2039/5158* (2013.01); *C12N 2501/599* (2013.01); *C12N 2501/998* (2013.01)

(58) Field of Classification Search
None
See application file for complete search history.

(56) References Cited

U.S. PATENT DOCUMENTS

2011/0014119 A1    1/2011    Jaiswal et al.

FOREIGN PATENT DOCUMENTS

| JP | 2011/519345 A | 7/2011 |
| WO | 1996/037107 A1 | 11/1996 |
| WO | 2009/091601 A1 | 7/2009 |
| WO | 2013/109752 A1 | 7/2013 |

OTHER PUBLICATIONS

Barrio et al., "Human Macrophages and Dendritic Cells Can Equally Present MART-1 Antigen to COB+ T Cells after1 Phagocytosis of Gamma-Irradiated Melanoma Cells", PLOS ONE, Jul. 2, 2012, pp. 1-12, vol. 7, No. 7, PLOS, San Francisco, CA.
Chao et al., "CD47-signal regulatory protein-a (SIRPa) interactions form a barrier for antibody-mediated tumorcell destruction", PNAS, Nov. 8, 2011, pp. 18342-18347, vol. 108, No. 45, National Academy of Sciences, Washington, D.C.
Chao et al., "The CD47-SIRPa Pathway in Cancer Immune Evasion and Potential Therapeutic Implications", Current Opinion in Immunology, Apr. 2012, pp. 225-232, vol. 24, Issue 2, Elsevier, New York City, NY.
Lei et al., "Induction of potent antitumor response by vaccination with tumor lysate-pulsed macrophages engineered tosecrete macrophage colony-stimulating factor and interferon-[gamma]", Gene Therapy, Apr. 1, 2000, pp. 707-713, vol. 7, No. 8, Macmillan Publishers Ltd., London, United Kingdom.
Prasad et al., "Dendritic Cells Loaded with Stressed Tumor Cells Elicit Long-Lasting Protective Tumor Immunity in Mice Depleted of CD4+CD25+ Regulatory T Cells", The Journal of Immunology, Jan. 1, 2005, pp. 1-10, vol. 174, Issue 1, The American Association of Immunologists, Inc., Rockville, MD.
Restifo et al., "Adoptive immunotherapy for cancer: harnessing the T cell response", Nat. Rev. Immunol., Apr. 1, 2012, pp. 269-281, vol. 12, Springer, Berlin, Germany.
Tseng et al., "Anti-CD47 antibody-mediated phagocylosis of cancer by macrophages primes an effective antitumor T-cell response", PNAS, May 20, 2013, pp. 11103-11108, vol. 110, No. 27, National Academy of Sciences, Washington, D.C.
Unanue, "Perspectives on anti-CD-47 antibody treatment for experimental cancer", PNAS, Jun. 19, 2013, pp. 10886-10887, vol. 110, No. 27, National Academy of Sciences, Washington, D.C.

*Primary Examiner* — Meera Natarajan
(74) *Attorney, Agent, or Firm* — Pamela J. Sherwood; Bozicevic, Field & Francis LLP

(57) ABSTRACT

Methods are provided for enhancing immunization strategies by manipulation, e.g. in vitro manipulation, of phagocytic antigen presenting cells. In the methods of the invention, phagocytic antigen presenting cells (phAPC) are incubated with a particulate antigen in the presence of an anti-CD47 agent in a dose and for a period of time sufficient to allow the phAPC to phagocytose the particulate antigen, which process generates a "loaded" phAPC. The loaded phAPC is contacted with a population of T cells matched for at least one major histocompatibility locus with the phAPC, where the T cells are stimulated after contacting to generate an effector response against an epitope or epitopes present on the particulate antigen.

5 Claims, 21 Drawing Sheets

Specification includes a Sequence Listing.

$\S\ p < 5 \times 10^{-6}$ $\ddagger\ p < 5 \times 10^{-5}$
$*\ p < 0.05$

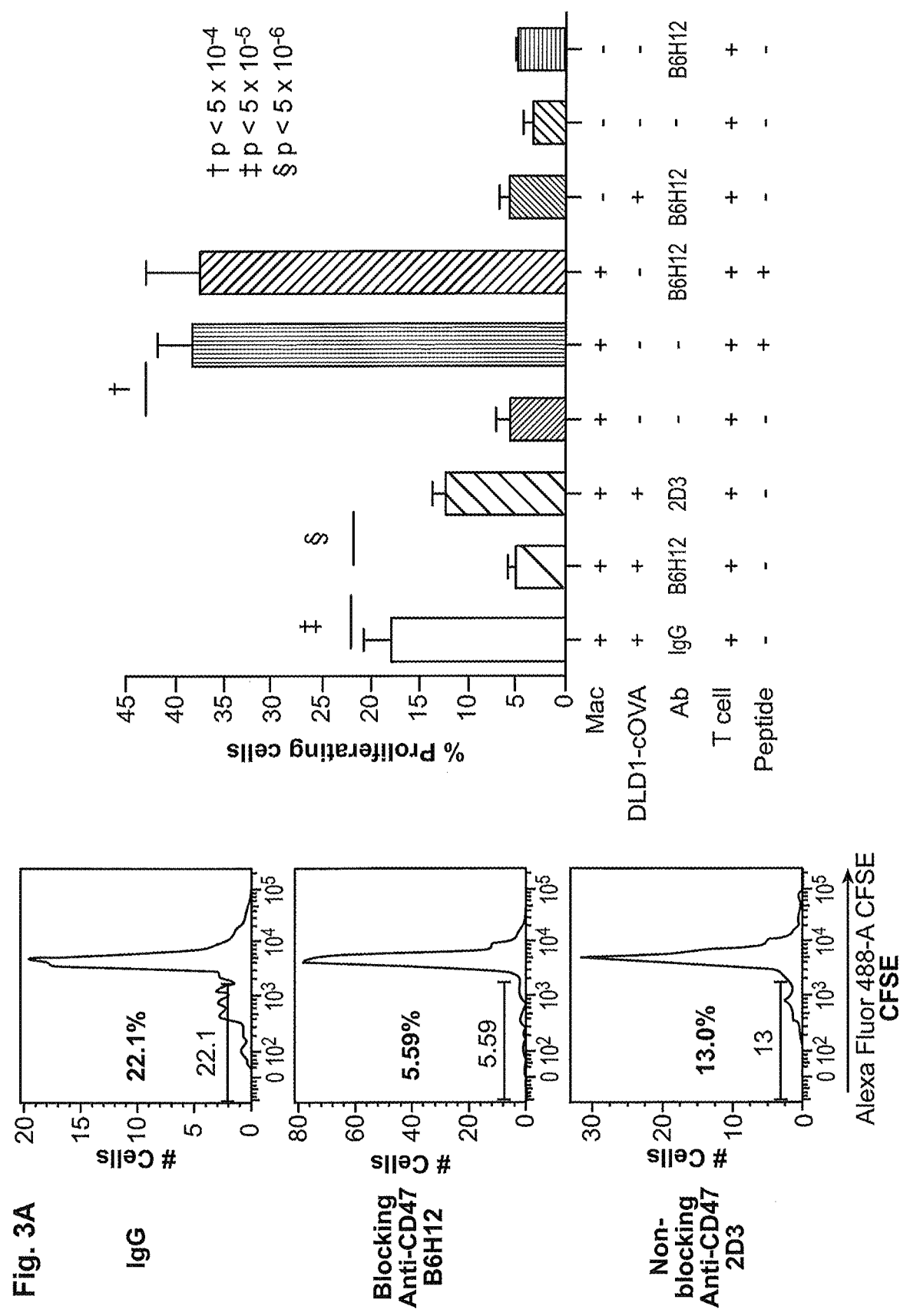

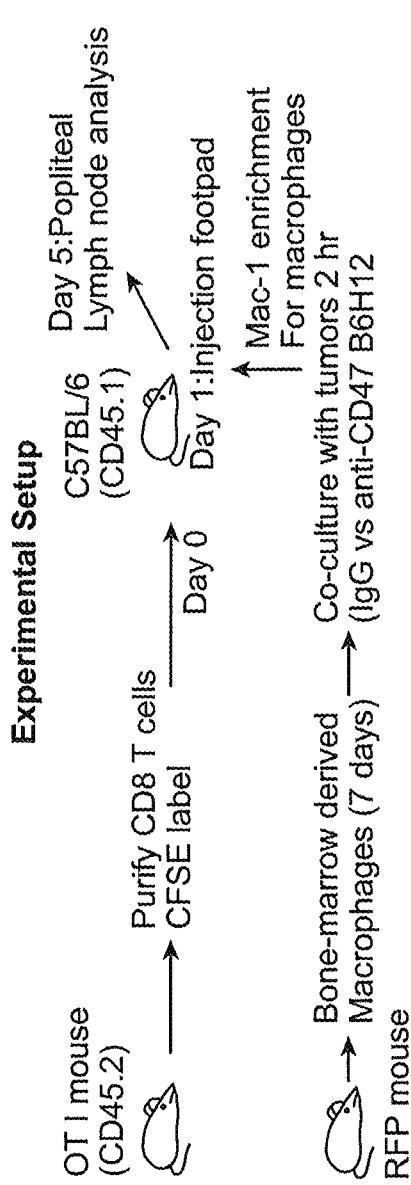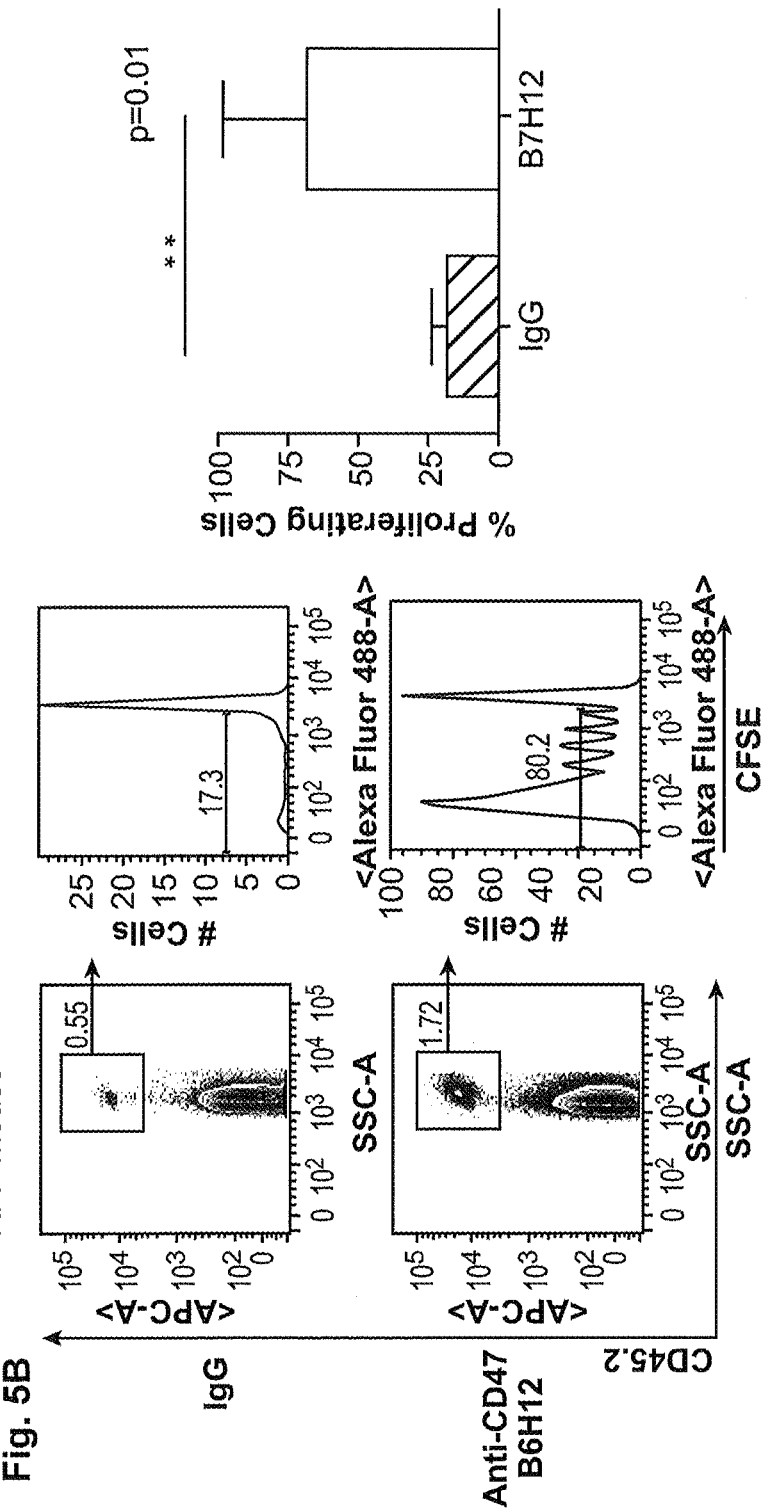
Fig. 5A
Fig. 5B

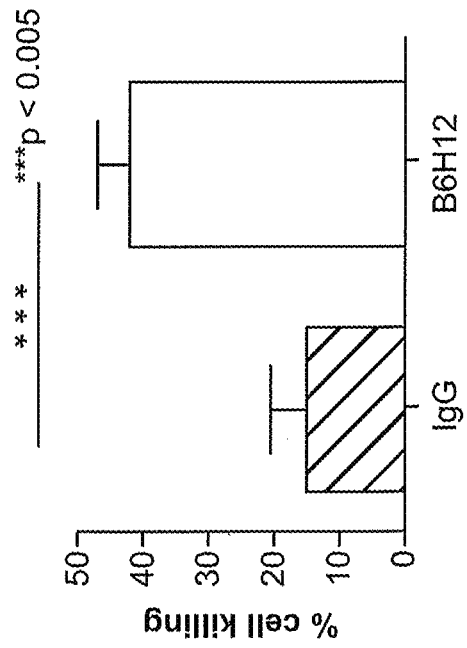
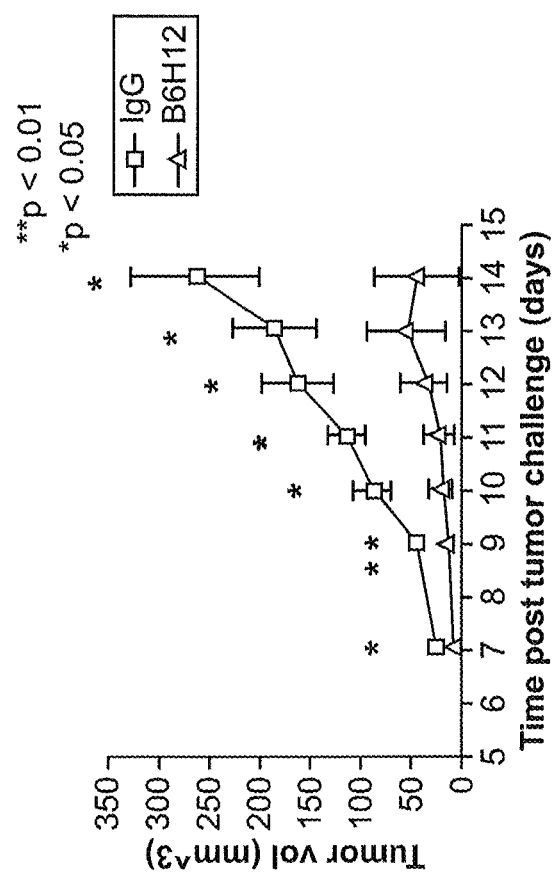
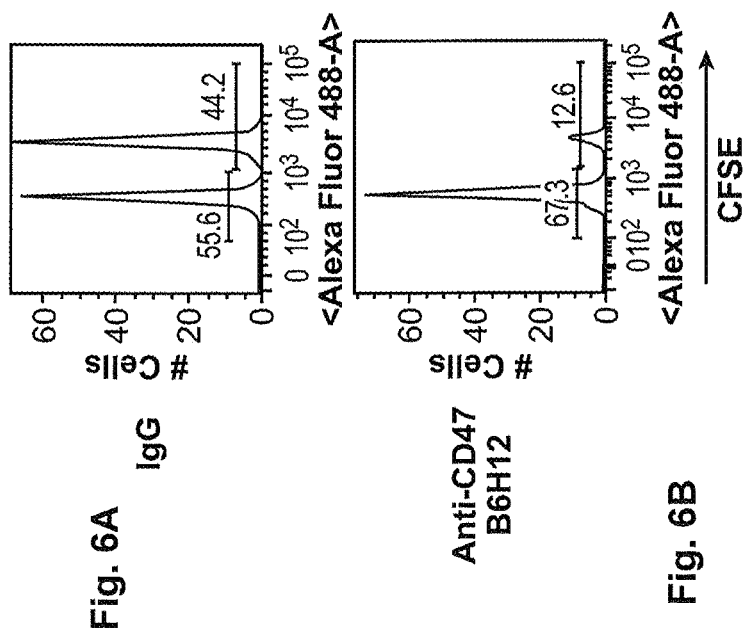
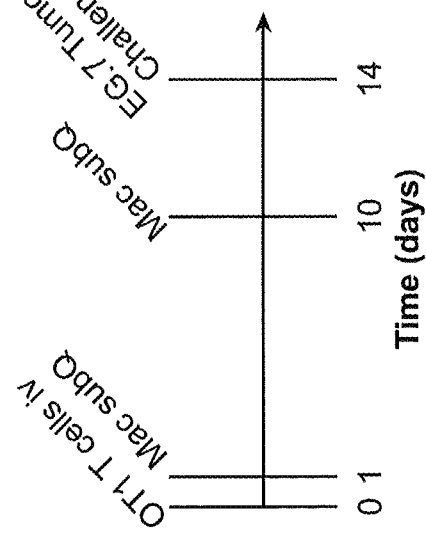
Fig. 6A
Fig. 6B

Macrophages, phagocytosis assay

IgG

Blocking anti-CD47 B6H12

Fig. 10A
Macrophages
Dendritic cells (DCs)
Fig. 10B
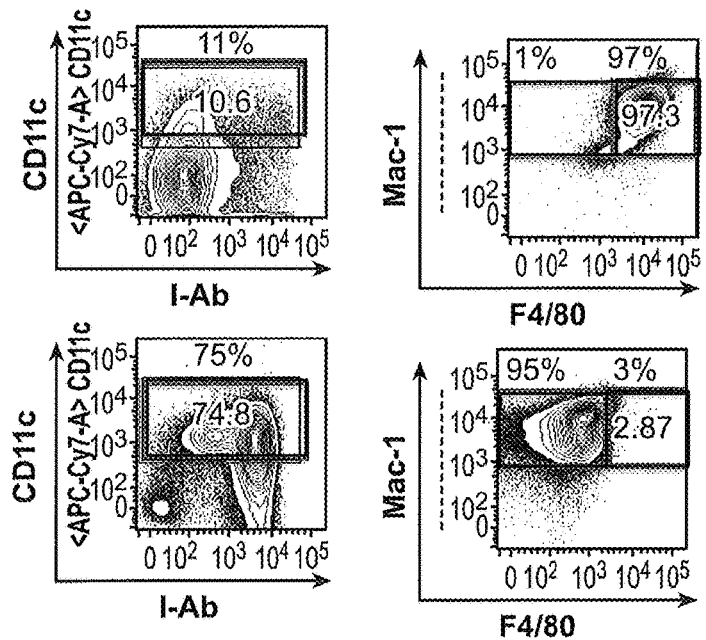
Fig. 10C
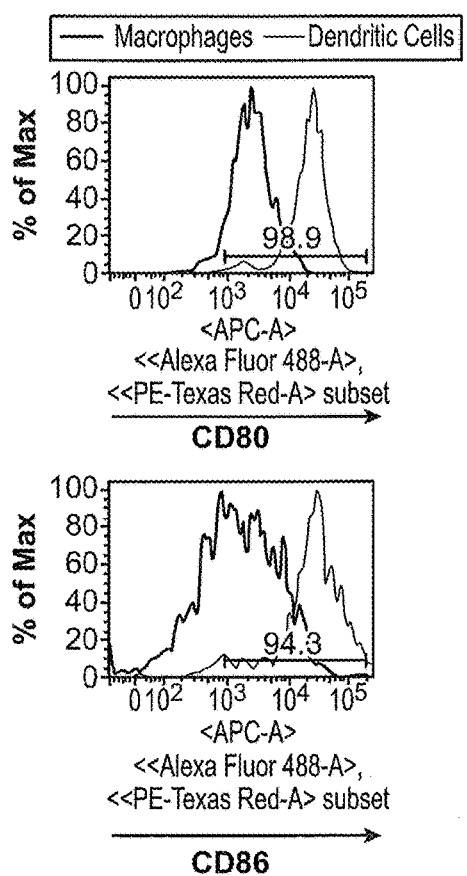
Fig. 10D
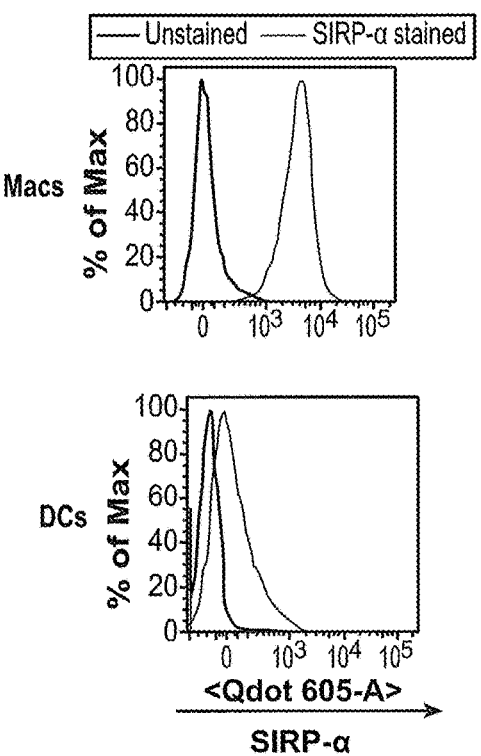

SEQUENCE LISTING

<160> NUMBER OF SEQ ID NOS: 1

<210> SEQ ID NO 1
<211> LENGTH: 8
<212> TYPE: PRT
<213> ORGANISM: Artificial
<220> FEATURE:
<223> OTHER INFORMATION: synthetic polypeptide

<400> SEQUENCE: 1

Ser Ile Ile Asn Phe Glu Lys Leu
1               5

USE OF ANTI-CD47 AGENTS TO ENHANCE IMMUNIZATION

CROSS REFERENCE

This application claims benefit and is a Continuation of application Ser. No. 14/786,898 filed Oct. 23, 2015, which is a 371 application and claims the benefit of PCT Application No. PCT/US2014/035167, filed Apr. 23, 2014, which claims benefit of U.S. Provisional Patent Application No. 61/817,229, filed Apr. 29, 2013, which applications are incorporated herein by reference in their entirety.

FEDERALLY SPONSORED RESEARCH AND DEVELOPMENT

This invention was made with Government support under contracts CA086017, CA139490, and CA168059 awarded by the National Institutes of Health. The Government has certain rights in the invention.

BACKGROUND OF THE INVENTION

Antigen presentation is the process by which innate immune cells like macrophages and dendritic cells (antigen presenting cells, APC) acquire antigens and present them to T cells to initiate the adaptive immune response. How APCs shape the immune response by both degrading antigens and preserving antigens for presentation to T cells has been a long-standing area of interest. Recently, the mechanism of antigen recognition by APCs has been shown to affect the preference of MHC I versus MHC II antigen presentation pathways. For instance, mannose receptor mediated endocytosis on dendritic cells has been shown to route antigens toward MHC I antigen presentation, whereas scavenger receptor-mediated endocytosis has been associated with MHC II presentation (Burgdorf et al (2007) *Science* 316 (5824):612-616).

Moreover, the functional outcomes of antigen presentation have been shown to be context-dependent. For instance, targeting antigens to DEC-205 using monoclonal antibodies induced tolerance under non-inflammatory conditions, but instead mediated immunogenicity under activating conditions by CD40L (Bonifaz et al. (2004) *J Exp Med* 199(6): 815-824). Harnessing APCs to enhance the anti-tumor T cell response offers an exciting strategy for cancer immunotherapy. The ability of the T cell immune response to be successfully mobilized against cancer has been demonstrated through preclinical and clinical studies of anti-CTLA4 antibody for T cell activation (Callahan et al. (2010) *Semin Oncol* 37(5):473-484).

CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2007) J.B.C. 282:14567-75; and the role of SIRPα cis dimerization in CD47 binding is discussed by Lee et al. (2010) J.B.C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

Phagocytosis by macrophages relies on the cell's recognition of pro-phagocytic ("eat me") and anti-phagocytic signals ("don't eat me") on a target cell. Blocking anti-CD47 monoclonal antibody (mAb) induces macrophage phagocytosis of cancer cells by inhibiting an important anti-phagocytic ("don't eat me") signal, allowing pro-phagocytic signals to dominate (Majeti et al. (2009) *Cell* 138(2):286-299; Willingham et al. (2012) *P.N.A.S.* 109(17):6662-6667). CD47 is highly expressed on cancer cells and pathogen-infected cells compared to normal cells, and interacts with the ligand SIRPα on macrophages. This results in phosphorylation of ITIM motifs on SIRPα's cytoplasmic tail and the recruitment of SHP-1 and SHP-2 phosphatases, which is thought to block phagocytosis by preventing myosin-IIA accumulation at the phagocytic synapse.

Therapeutic efficacy of blocking anti-CD47 mAbs against xenograft human cancers growing in immunodeficient mice, including cancers such as leukemia, lymphoma, multiple myeloma, and solid tumors, including breast, colon, prostate, bladder cancers, and sarcomas has been demonstrated. Whether the adaptive immune response can also be recruited against the cancer following anti-CD47 mAb treatment has not been determined.

SUMMARY OF THE INVENTION

Methods are provided for enhancing immunization strategies by manipulation, e.g. in vitro manipulation, of phagocytic antigen presenting cells. In the methods of the invention, phagocytic antigen presenting cells (phAPC), including without limitation macrophages, are incubated with a particulate antigen in the presence of an anti-CD47 agent in a dose and for a period of time sufficient to allow the phAPC to phagocytose the particulate antigen, which process generates a "loaded" phAPC. The loaded phAPC is contacted with a population of T cells matched for at least one major histocompatibility locus with the phAPC, where the T cells are stimulated after contacting to generate an effector response against an epitope or epitopes present on the particulate antigen.

In some embodiments of the invention, the particulate antigen is a cell (which may be referred to herein as a target cell), for example a mammalian cell infected with an intracellular pathogen such as a virus, an intracellular bacteria, an intracellular protozoan, etc.; a mammalian tumor cell such as a carcinoma, glioma, sarcoma, melanoma, myeloma, leukemia, lymphoma, etc., including without limitation the hematologic cancers AML, CML, ALL, NHL, multiple myeloma, etc., and solid tumors, including breast, colon, prostate, bladder cancers, gliomas, sarcomas, and the like. The target cell generally expresses CD47 or a CD47 mimic.

An anti-CD47 agent useful in the methods of the invention interferes with binding between CD47 present on the target cell and SIRPα present on the phAPC. Suitable anti-CD47 agents include soluble SIRPα polypeptides; soluble CD47; anti-CD47 antibodies, anti-SIRPα antibodies, and the like, where the term antibodies encompasses antibody fragments and variants thereof, as known in the art.

Suitable phagocytic antigen presenting cells have the characteristics of being (a) capable of phagocytosis of the particulate antigen, particularly where the particulate antigen is a mammalian cell; (b) express SIRPα; (c) capable of presenting antigen to a T cell, including without limitation the ability to stimulate directly or indirectly an antigen-specific response by cytotoxic T cells. Examples of such phAPC are dendritic cells and macrophages. The phAPC can be isolated from a mammalian donor, or matured in vitro from a progenitor cell, e.g. from monocytes, peripheral blood mononuclear cells, and the like as known in the art.

The phAPC is selected to share at least one major histocompatibility complex (MHC) protein with the intended population of T cells. In some embodiments the phAPC is autologous to the intended T cell population. In some embodiments the phAPC is allogeneic, but sharing at least one MHC protein, for example at least one Class II MHC protein, including without limitation the human proteins HLA-DM; HLA-DO; HLA-DP; HLA-DQ; HLA-DR. Alternatively or in combination the phAPC and target T cells share at least one MHC Class I allele, including without limitation HLA-A, HLA-B. In certain such embodiments the phAPC is at least matched for one HLA-DR allele, and may be matched for both HLA-DR alleles. In some embodiments the phAPC is matched at 2, 3, 4, 5, 6, 7, 8, 9, 10 HLA proteins. It is known to those of skill in the art that each HLA Class II protein is comprised of two polypeptides, each of which can be polymorphic in sequence.

T cells responsive to the phAPC can be helper T cells, e.g. TH1, TH2, TH17, etc., regulatory T cells, e.g. FoxP3+ cells; or cytotoxic T cells (CTL), e.g. CD8+ T cells. Preferred T cells are effector CTL cells. The T cells can be contacted in vitro or in vivo. Where the contacting is in vitro, the population of loaded phAPC are mixed with a candidate T cell population, which is optionally enriched for the T cell subset of interest and incubated for a period of time sufficient to activate the T cells. Where the contacting is performed in vivo, the population of phAPC is injected into the recipient mammal at a site that provides for access to lymph nodes, e.g. intravenous, sub-cutaneous, intratumoral, and the like. Where the contacting is performed in vitro, suitable culture medium is used, optionally including cytokines.

Kits for practice of the invention are also provided. Such kits may comprise one or more of an anti-CD47 agent; reagents for selection or in vitro maturation of phAPC; particulate antigen or reagents for selection of target cells; in addition to buffers, cell culture medium, growth factors, and disposables such an syringes, tissue culture dishes, and the like. Kits may also include instructions for use.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

(FIG. 1A) RFP+ macrophages were co-cultured with DLD1-cOVA-GFP cancer cells in the presence of IgG or anti-CD47 mAbs B6H12 (blocking) or 2D3 (non-blocking). Percentage phagocytosis was determined by % GFP$^+$ within RFP$^+$ macrophage cell gate. (FIG. 1B) RFP$^+$ macrophages versus dendritic cells were co-cultured with DLD1-cOVA-GFP cancer cells in the presence of IgG, anti-CD47 B6H12, or anti-CD47 2D3 mAbs. Experiment was performed three times with similar results.

(FIG. 2A) RFP+ macrophages were co-cultured with human DLD1-cOVA-GFP cells in the presence of IgG, anti-CD47 B6H12 (blocking), or anti-CD47 2D3 (non-blocking) mAbs. The following day, CD8$^+$ T cells were magnetically enriched from OTI transgenic mice and labeled with CFSE (0.5 uM). Analysis was performed on day 3 and % proliferating cells determined. Macrophages were pulsed with OT-I peptide (SIINFEKL, SEQ ID NO:1), OVA257-264 as a positive control. Experiment was performed three times with similar results. (FIG. 2B) RFP$^+$ macrophages were co-cultured with DLD1-cOVA-GFP cancer cells or DLD1-GFP cancer cells not expressing cOVA. (Left) Phagocytosis was determined by % GFP$^+$ within RFP$^+$ macrophage cell gate. (Right) CFSE-labeled CD8+ T cells from OT-I mice were added to cultures and % proliferating cells was determined.

FIG. 3A-3B. Following phagocytosis of cancer cells by anti-CD47, macrophages do not prime CD4$^+$ T cells to proliferate. (FIG. 3A) RFP$^+$ macrophages were cocultured with DLD1-cOVA-GFP cancer cells in the presence of IgG, anti-CD47 B6H12 (blocking), or anti-CD47 2D3 (non-blocking) mAbs. The following day, CD4$^+$ T cells were isolated from OT-II transgenic mice and labeled with CFSE (0.5 µM). Analysis was performed on day 4, and % proliferating cells determined. Macrophages were pulsed with OVA peptide 323-339 as a positive control. (FIG. 3B) RFP$^+$ macrophages were stimulated with IFN-γ to upregulate MHC II levels. Phagocytosis and priming of OT-II CD4$^+$ cells were determined in the presence of anti-CD47 mAbs.

FIG. 5A-5B. Following anti-CD47 mediated phagocytosis of cancer cells, macrophages prime CD8$^+$ T cells in vivo. (FIG. 5A) Experimental setup. (FIG. 5B) Adoptively transferred CFSE$^+$ OT-I T cells were analyzed in the draining lymph node by gating on CD45.2$^+$ cells. % proliferating cells were determined by gating on the CFSE-low population. N=5 mice per group.

FIG. 6A-6B. Following anti-CD47-mediated phagocytosis of cancer cells, macrophages prime an anti-tumor CD8$^+$ T cell response in vivo. (FIG. 6A) Following anti-CD47-mediated phagocytosis of cancer cells, macrophages prime effector cytotoxic T cells. CD8$^+$ T cells were isolated from OT-I transgenic mice and transferred iv to recipient mice. Macrophages were co-cultured with DLD1-cOVA-GFP tumors in vitro in the presence of IgG or blocking anti-CD47 B6H12 mAbs. Macrophages were isolated by magnetic separation and then transferred subcutaneously the following day. After four days, target cells (CD45.1 splenocytes) were CFSE labeled high (10 µM) or low (1 µM). CFSE high cells were pulsed with 1 µM OVA class I-restricted peptide (SIINFEKL, SEQ ID NO:1) to make them targets for OT-I cytotoxic T cell function. CFSE high (peptide-pulsed) and low cells (unpulsed) were mixed in a 1:1 ratio and transferred intravenously. Draining lymph nodes were analyzed 16 hours later to determine the percentage of CFSE high versus CFSE low cells. Percentage of cell killing was determined according to materials and methods. N=10 mice. (FIG. 6B) Following anti-CD47-mediated phagocytosis of tumors, macrophages prime an anti-tumor CD8 T cell response. OT-I CD8$^+$ T cells were transferred intravenously to recipient mice. Macrophages were co-cultured with DLD1-cOVA-GFP cancer cells in vitro in the presence of IgG or anti-CD47 B6H12 mAbs, and then macrophages transferred subQ on days 1 and 10. Animals were challenged with EG.7 cancer cells on day 14, and tumor growth monitored over time. N=5 mice per group.

(FIG. 7A) IC-21 macrophage cell line was transfected with a lentivirus expressing cytoplasmic ovalbumin and GFP from the EF-1 promoter. Macrophages were profiled for expression of SIINFEKL-H2kb (SEQ ID NO:1). (FIG. 7B) DLD1 cell lines were transfected with lentivirus expressing GFP only or cytoplasmic ovalbumin and GFP. Ovalbumin protein expression was confirmed by western blot. (FIG. 7C) Both anti-CD47 mAbs, clones B6H12 (blocking) and 2D3 (non-blocking), bind to the cell surface of DLD1-cOVA-GFP cancer cells.

(FIG. 8A) Macrophages generated from wild-type C57BL/6 mice and RFP macrophages generated from C57BL/Ka Rosa26-mRFP1 transgenic mice phagocytose tumors in the presence of anti-CD47 B6H12 at similar levels. (FIG. 8B) Representative macrophage phagocytosis of tumors in the presence of anti-CD47 antibody is shown using Wright-Giemsa stain.

FIG. 10A-10D. Characterization of in vitro-derived macrophages and dendritic cells. (FIG. 10A) Macrophages and dendritic cell morphologies are shown using Wright-Giemsa stain. (FIG. 10B) Macrophages are predominantly $Mac1^+$ $F4/80^+$. Dendritic cells are predominantly $CD11c^+$. (FIG. 10C) Dendritic cells express higher levels of co-stimulatory molecules CD80 and CD86 than macrophages. (FIG. 10D) Macrophages express SIRPα at high levels, whereas dendritic cells express SIRPα at lower levels.

(FIG. 11A) Following phagocytosis of tumors by anti-CD47 antibody, macrophages upregulate expression levels of MHC II (I-Ab) (FIG. 11B) Following phagocytosis of tumors by anti-CD47 antibody, macrophages increase levels of costimulatory molecule CD86, but not coinhibitory molecule B7-H1.

(FIG. 12A) Left: OT-II/Foxp3-GFP express GFP within CD4+ CD25+ gate in the peripheral blood. Right: OT-II/Foxp3-GFP mice express an increased frequency of Vα2 restricted TCR. (FIG. 12B) CD4+ T cells were enriched from peripheral lymph nodes of OT-II/Foxp3-GFP mice and co-cultured in the presence of RFP macrophages. Foxp3-GFP+ cells were induced in the presence of TGF-β (20 ng/mL) and all-trans-retinoic acid (RA) (1 nM).

DETAILED DESCRIPTION OF THE INVENTION

Figure 1A:
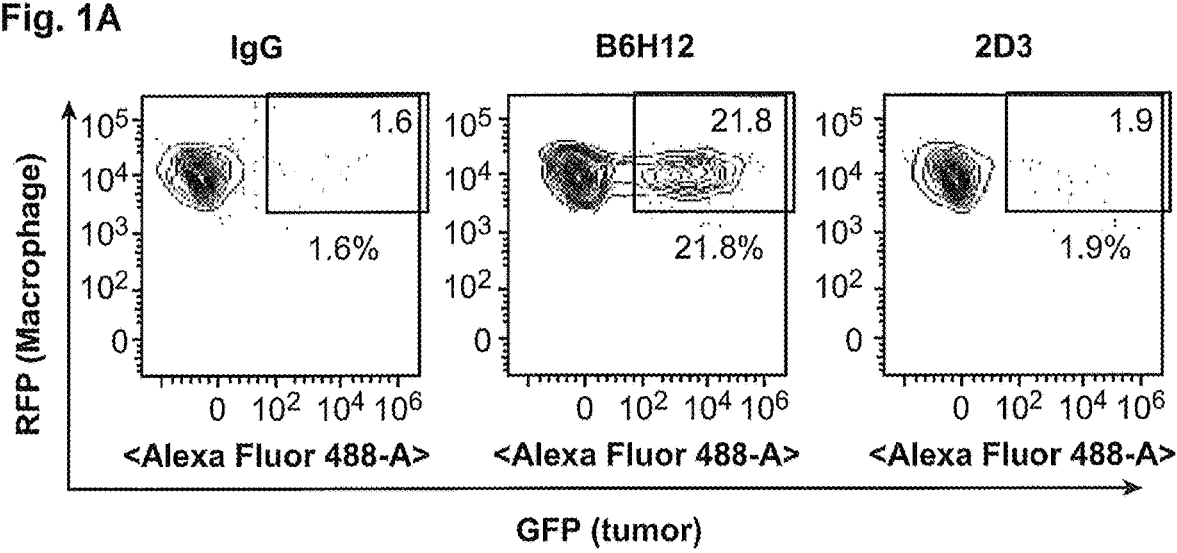
FIG. 1A-1B. Macrophages efficiently phagocytose cancer cells in the presence of anti-CD47 B6H12 antibody.
Figure 1A:
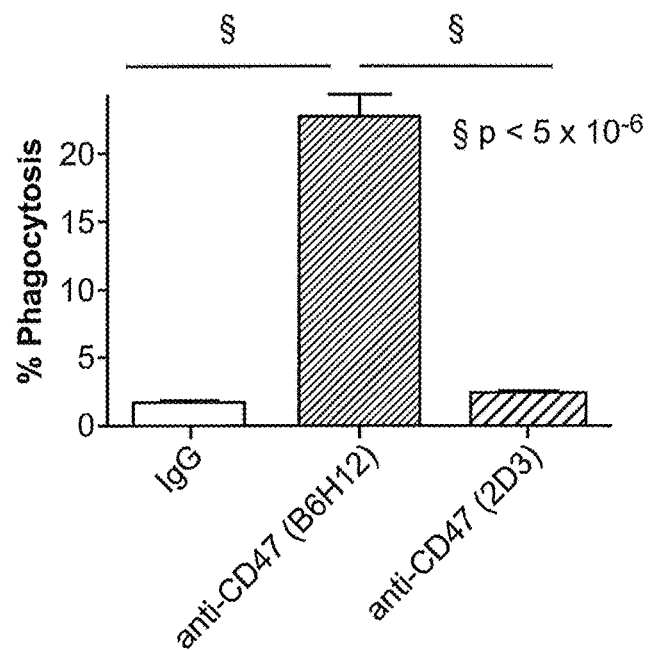
Figure 1B:
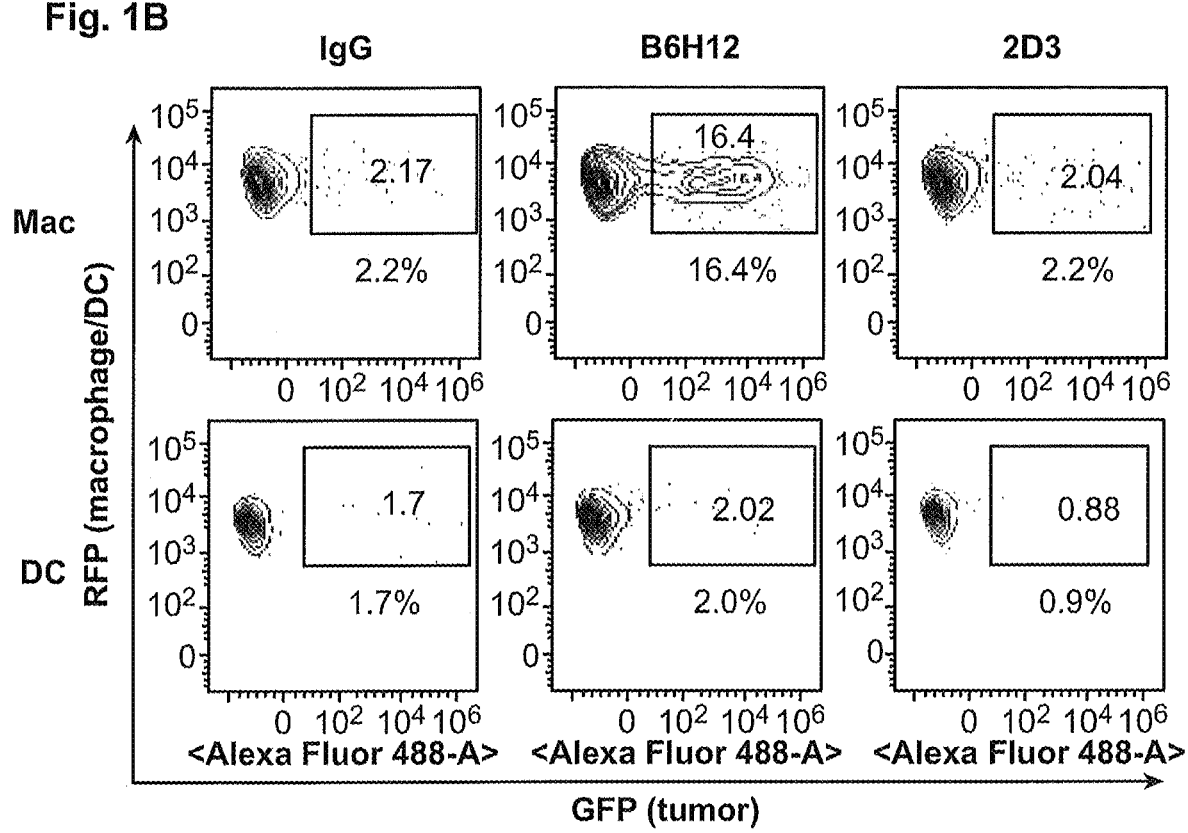
Figure 1B:
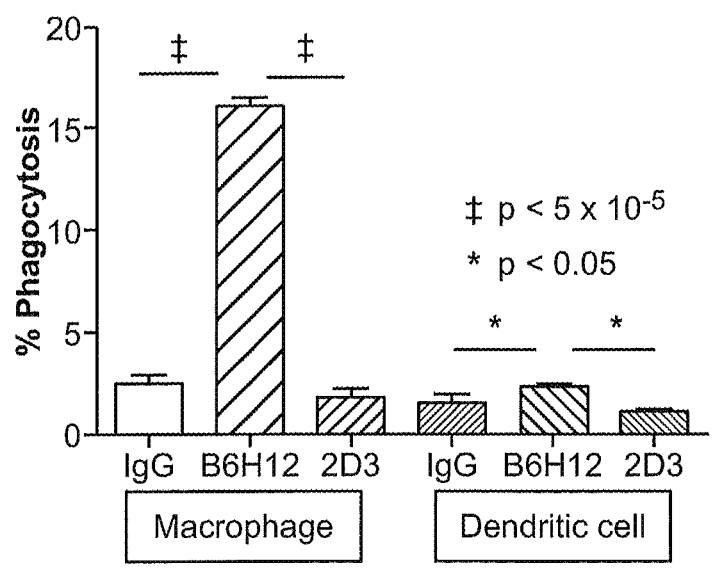

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Anti-CD47 agent. As used herein, the term "anti-CD47 agent" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies, antibody fragments, peptides, small molecules, peptidomimetics, and the like. In some embodiments, a suitable anti-CD47 agent (e.g. an anti-CD47 antibody, a SIRPα reagent, etc.) specifically binds CD47 to reduce the binding of CD47 to SIRPα. In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell).

The efficacy of a suitable anti-CD47 agent can be assessed by assaying the agent. In an exemplary assay, target cells are incubated in the presence or absence of the candidate agent. An agent for use in the methods of the invention will up-regulate phagocytosis and subsequent T cell activation by at least 10% (e.g., at least 20%, at least 30%, at least 40%, at least 50%, at least 60%, at least 70%, at least 80%, at least 90%, at least 100%, at least 120%, at least 140%, at least 160%, at least 180%, or at least 200%) compared to phagocytosis and subsequent T cell activation in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) may occur (Manna and Frazier (2004) Cancer Research 64:1026-1036). Thus, in some embodiments, the anti-CD47 agent does not directly induce cell death of a CD47-expressing cell.

Some pathogens (e.g., pox viruses, Myxoma virus, Deerpox virus, swinepox virus, goatpox virus, sheeppox virus, etc.) express a CD47-analog (i.e., a CD47 mimic) (e.g., the M128L protein) that acts as a virulence factor to enable infection (Cameron et al., *Virology.* 2005 Jun. 20; 337(1): 55-67), and some pathogens induce the expression of endogenous CD47 in the host cell. Cells infected with a pathogen that expresses a CD47-analog may therefore express the pathogen-provided CD47 analog either exclusively or in combination with endogenous CD47. This mechanism allows the pathogen to increase CD47 expression (via expression of the CD47 analog) in the infected cell with or without increasing the level of endogenous CD47. In some embodiments, an anti-CD47 agent (e.g., anti-CD47 antibody, a SIRPα reagent, a SIRPα antibody, a soluble CD47 polypeptide, etc.) can reduce the binding of a CD47 analog (i.e., a CD47 mimic) to SIRPα. In some cases, a suitable anti-CD47 agent (e.g., a SIRPα reagent, an anti-CD47 antibody, etc.) can bind a CD47 analog (i.e., a CD47 mimic) to reduce the binding of the CD47 analog to SIRPα. In some cases, a suitable anti-CD47 agent (e.g., an anti-SIRPα antibody, a soluble CD47 polypeptide, etc.) can bind to SIRPα. A suitable anti-CD47 agent that binds SIRPα does not activate SIRPα (e.g., in the SIRPα-expressing phagocytic cell). An anti-CD47 agent can be used in any of the methods provided herein when the pathogen is a pathogen that provides a CD47 analog. In other words the term "CD47," as used herein, encompasses CD47 as well as CD47 analogs (i.e., CD47 mimics).

SIRPα Reagent.

A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα. In some embodiments, a SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

In some embodiments, a subject anti-CD47 agent is a "high affinity SIRPα reagent", which includes SIRPα-derived polypeptides and analogs thereof. High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

Anti-CD47 Antibodies.

In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Nonlimiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Anti-SIRPα antibodies. In some embodiments, a subject anti-CD47 agent is an antibody that specifically binds SIRPα (i.e., an anti-SIRPα antibody) and reduces the interaction between CD47 on one cell and SIRPα on another cell. Suitable anti-SIRPα antibodies can bind SIRPα without activating or stimulating signaling through SIRPα, because activation of SIRPα would inhibit phagocytosis. Instead, suitable anti-SIRPα antibodies facilitate the phagocytosis of target cells. Thus, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 Polypeptides.

In some embodiments, a subject anti-CD47 agent is a soluble CD47 polypeptide that specifically binds SIRPα and reduces the interaction between CD47 on one cell and SIRPα on another cell. A suitable soluble CD47 polypeptide can bind SIRPα without activating or stimulating signaling through SIRPα. Suitable soluble CD47 polypeptides facilitate the phagocytosis of target cells. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

In certain embodiments, soluble CD47 polypeptide comprises the extracellular domain of CD47, including the signal peptide, such that the extracellular portion of CD47 is typically 142 amino acids in length. The soluble CD47 polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPα without stimulating SIRPα signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide. As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPα without stimulating SIRPα signaling. The CD47 extracellular domain variant may have an amino acid sequence that is at least 65%-75%, 75%-80%, 80-85%, 85%-90%, or 95%-99% identical (which includes any percent identity between any one of the described ranges) to the extracellular domain of CD47.

Phagocytic antigen presenting cell. The terms "phagocytic cells" and "phagocytes" are used interchangeably herein to refer to a cell that is capable of phagocytosis, i.e. engulfing a large particulate mass, for example from about 0.1 µm in diameter up to about 2 mm or about 1 mm in diameter; from about 0.5 µm in diameter in to about 1 mm in diameter, etc, particularly including up to the size of a mammalian cell, e.g. a tumor cell. Phagocytosis in this context is defined by the engulfment of cells, pathogens, and various particles by surrounding it with the effector cell membrane.

There are several categories of phagocytes: macrophages; mononuclear cells (histiocytes and monocytes); polymorphonuclear leukocytes; (neutrophils) and dendritic cells. Macrophages are of particular interest. Phagocytosis-associated cell responses include immunomodulatory responses like the generation and release of pro-inflammatory and anti-inflammatory mediators, and also cell responses of destructive nature such as the respiratory burst, and the release of toxic and microbicidal molecules by degranulation. Professional phagocytes are capable of recognizing a wide variety of phagocytic targets, and of ingesting them at a higher rate than non-phagocytic cells.

Neutrophils and macrophages are representative of fully differentiated phagocytes. While neutrophils leaving the bone marrow are fully differentiated, macrophages differentiate from circulating monocytes in extra-vascular tissues. Monocytes display a lower phagocytic response, compared to neutrophils and macrophages, and must respond to activation and differentiation signals in order to achieve optimal phagocytic capacity. The process of monocyte-to-macrophage differentiation has been well characterized, and can be performed in vitro or in vivo.

Dendritic cell (DC) refers to any member of a diverse population of morphologically similar cell types found in lymphoid or non-lymphoid tissues. DCs are referred to as "professional" antigen presenting cells, and have a high capacity for sensitizing MHC-restricted T cells. DCs may be recognized by function, by phenotype and/or by gene expression pattern, particularly by cell surface phenotype. These cells are characterized by their distinctive morphology, high levels of surface MHC-class II expression and ability to present antigen to $CD4^+$ and/or $CD8^+$ T cells, particularly to naïve T cells (Steinman et al. (1991) *Ann. Rev. Immunol.* 9:271; incorporated herein by reference for its description of such cells).

Immature DCs express low levels of MHC class II, but are capable of endocytosing antigenic proteins and processing them for presentation in a complex with MHC class II molecules. Activated DCs express high levels of MHC class II, ICAM-1 and CD86, and are capable of stimulating the proliferation of naïve allogeneic T cells, e.g. in a mixed leukocyte reaction (MLR). Functionally, DCs may be identified by any convenient assay for determination of antigen presentation. Such assays may include testing the ability to stimulate antigen-primed and/or naïve T cells by presentation of a test antigen, followed by determination of T cell proliferation, release of IL-2, and the like.

Typical protocols for in vitro differentiation of macrophages or dendritic cells from monocytes are described, for example, in Davies and Gordon, Methods in Molecular Biology vol. 290: Basic Cell Culture Protocols, Third edition; and Zhang et al. (2008) Curr. Protoc. Immunology November, each herein specifically incorporated by reference. Such methods generally utilize mononuclear cells from peripheral blood (PBMC), which can be enriched by selection for cells bearing monocyte markers or by adherence, for example to a culture dish, although such enrichment is not required. Markers for macrophages include F4/80, CD11 b and CD68. Such methods usually take advantage of the use of macrophage colony-stimulating factor (M-CSF) and/or IL-4 to differentiate macrophage progenitor cells from the bone marrow or peripheral blood into mature macrophages in culture, yielding a homogenous population of macrophages in a relatively quiescent state that are responsive to activation stimuli in vitro.

For example, bone marrow cells or peripheral blood cells are harvested and cultured in the medium containing M-CSF. After 7 days in culture, contaminating nonadherent cells are eliminated and adherent cells are harvested for assays. Adherent bone marrow or peripheral blood-derived macrophages are usually better than 90% pure. Alternatively monocytes can be derived from more primitive progenitors, such as hematopoietic stem cells, ES cells, iPS cells and the like.

Specialized antigen-presenting cells (APCs) take up external proteins, digest those proteins into short peptides, and present the peptides bound to MHC molecules, e.g. Class I or Class II HLA. T cells bind to the peptide-MHC complexes presented on the surfaces of APCs if they have matching TCRs. Various co-stimulatory molecules may be involved, e.g. CD80 and CD86, and/or ICOS-L expressed by the APC. It is a feature of APC that they stimulate an antigen-specific response by T cells, particularly by naïve T cells.

In certain embodiments, the phAPC or precursors thereof are frozen in liquid nitrogen (or equivalent) prior to use. For example, the tissue source (e.g., bone marrow, peripheral blood) may be harvested, frozen and stored until needed. Likewise, phAPC derived in vitro from precursors can be frozen and stored until used. If frozen, the cells will usually be stored in a 10% DMSO, 50% FCS, 40% RPMI 1640 medium in liquid nitrogen.

The phAPC and the T cells that are of interest for priming are selected to share at least one MHC antigen. Major histocompatibility complex antigens (also called human leukocyte antigens, HLA) are protein molecules expressed on the surface of cells that confer a unique antigenic identity to these cells. MHC/HLA antigens are target molecules that are recognized by T-cells and natural killer (NK) cells as being derived from the same source of cells as the immune effector cells ("self"). Two main classes of HLA antigens are recognized: HLA class I and HLA class II. HLA class I antigens (A, B, and C in humans) render each cell recognizable as "self," whereas HLA class II antigens (DR, DP, and DQ in humans) are involved in reactions between lymphocytes and antigen presenting cells.

An important aspect of the HLA gene system is its polymorphism. Each gene, MHC class I (A, B and C) and MHC class II (DP, DQ and DR) exists in different alleles. HLA alleles are designated by numbers and subscripts. For example, two unrelated individuals may carry class I HLA-B, genes B5, and Bw41, respectively. Allelic gene products differ in one or more amino acids in the α and/or β domain(s). Large panels of specific antibodies or nucleic acid reagents are used to type HLA haplotypes of individuals, using leukocytes that express class I and class II molecules. The genes most important for HLA typing are the six MHC Class I and Class II proteins, two alleles for each of HLA-A; HLA-B and HLA-DR.

The human leukocyte antigen (HLA) genes are clustered in a "super-locus" present on chromosome position 6p21, which encodes the six classical transplantation HLA genes and at least 132 protein coding genes that have important roles in the regulation of the immune system as well as some other fundamental molecular and cellular processes. The complete locus measures roughly 3.6 Mb, with at least 224 gene loci. One effect of this clustering is that "haplotypes", i.e. the set of alleles present on a single chromosome, which is inherited from one parent, tend to be inherited as a group. The set of alleles inherited from each parent forms a haplotype, in which some alleles tend to be associated together. Identifying a patient's haplotypes can help predict the probability of finding matching donors and assist in developing a search strategy, because some alleles and haplotypes are more common than others and they are distributed at different frequencies in different racial and ethnic groups.

HLA alleles are typically noted with a variety of levels of detail. Most designations begin with HLA- and the locus name, then * and some (even) number of digits specifying the allele. The first two digits specify a group of alleles. Older typing methodologies often could not completely distinguish alleles and so stopped at this level. The third through fourth digits specify a synonymous allele. Digits five through six denote any synonymous mutations within the coding frame of the gene. The seventh and eighth digits distinguish mutations outside the coding region. Letters such as L, N, Q, or S may follow an allele's designation to specify an expression level or other non-genomic data known about it. Thus, a completely described allele may be up to 9 digits long, not including the HLA-prefix and locus notation.

Any method known in the art may be optionally used to for typing the cells. For example, three main processes are currently used to perform HLA typing. The first is conventional serological cytotoxicity method, where samples of lymphocytes (taken from blood or spleen) are added to Terasaki plates. These plates hold individual wells that contain different specific antibodies (from either maternal sera or manufactured monoclonal antibodies). The best cells for class II typing are B lymphocytes, and class I typing can be performed with the remaining leucocytes. Magnetic beads are used to purify the required cells from blood or spleen. If the HLA antigen and specific antibody bind, and complement is added, the cells in that well is killed. The pattern of wells showing this cell death allows the deduction of which combination of HLA antigens were present on the original tissue cells.

Another method used for HLA typing is flow cytometry, particularly when looking for specific alleles. Leucocytes are added to detectable labeled monoclonal antibodies specific for the HLA types of interest. The sample is then analyzed by flow cytometry to determine which antibodies have bound to the cells.

DNA typing is increasingly being used for HLA typing. This process involves extracting the DNA from cells and amplifying the genes that encode for the HLA peptides using polymerase chain reaction techniques. The genes may be matched with known HLA nucleotide sequences found stored in several gene bank databases, including the IMGT/HLA database.

A "therapeutically effective dose" or "therapeutic dose" is an amount sufficient to effect desired clinical results (i.e., achieve therapeutic efficacy). For some purposes in the present invention, an effective dose of an anti-CD47 agent is the dose that enhances the ability of a phAPC to become loaded with a particulate antigen, e.g. by increasing phagocytosis by at least about 10%, at least about 20%, at least about 50%, at least about 75%, at least about 100%, up to 2-fold, 3-fold or more. For example, the phAPC may be combined with particulate antigen in medium comprising at least 0.01 µg/ml, at least 0.1 µg/ml, at least 1 µg/ml, at least 10 µg/ml or more of an anti-CD47 agent. A loaded phAPC population may have phagocytosed on average at least about 0.1, 0.2, 0.5, 0.75, 1 antigen particles, e.g. tumor cells, virus infected cells, etc. per APC.

A therapeutically effective dose of loaded phAPC is that dose effective to increase targeted, i.e. antigen-specific response by T cells in vivo. The response may, in some cases, be directed against diverse epitopes of tumor-specific, virus-specific, bacteria-specific, etc. antigens. As such, it may be more convenient to determine dose in terms of the killing of the targeted cells.

For purposes of this invention, a therapeutically effective dose of an anti-CD47 agent is an amount that is sufficient to palliate, ameliorate, stabilize, reverse, prevent, slow or delay the progression of the disease state (e.g., cancer or chronic infection) by increasing T cell mediated killing of a target cell (e.g., a target cell) or T cell mediated damage that eventually results in cell death. Thus, a therapeutically effective dose of an anti-CD47 agent can decrease the target cell population through an in vivo immune response by at least about 10%, at least about 20%, at least about 50%, at least about 75%, at least about 90% or more, relative to the effect in the absence of administering a loaded population of phAPC.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, etc.) as well as those in which prevention is desired (e.g., those with increased susceptibility to cancer, those with an increased likelihood of infection, those suspected of having cancer, those suspected of harboring an infection, etc.).

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

As used in this invention, the term "epitope" means any antigenic determinant on an antigen to which an antibody binds, or against which a T cell response is directed through binding of the T cell antigen receptor. Epitopic determinants usually consist of chemically active surface groupings of molecules such as amino acids or sugar side chains and usually have specific three dimensional structural characteristics, as well as specific charge characteristics.

Particulate Antigen.

As used herein a particulate antigen is an antigen of a size that requires a phagocytic cell to engulf, e.g. large beads, etc. In most instances the particulate antigen is a cell, particularly a mammalian cell and including human cells as well as other mammals. For example, a cell may be a tumor cell, an infected cell, etc. In some embodiments the cell is obtained or derived from the recipient, e.g. a tumor biopsy, sample of infected cells, etc. The response by T cells is ultimately directed to epitopes associated with the cell, e.g. tumor-specific or virus-specific proteins.

Examples of tumor cells include but are not limited to AML, ALL, CML, adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, Hodgkin's lymphoma, Kaposi's sarcoma, kidney cancer, laryngeal and hypopharyngeal cancer, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g. uterine sarcoma), transitional cell carcinoma, vaginal cancer, vulvar cancer, mesothelioma, squamous cell or epidermoid carcinoma, bronchial adenoma, choriocarcinoma, head and neck cancers, teratocarcinoma, or Waldenstrom's macroglobulinemia. Any cancer, where the cancer cells exhibit increased expression of CD47 compared to non-cancer cells, is a suitable cancer to be treated by the subject methods and compositions.

In other embodiments the target cell is infected with a pathogen. As used herein, the term "infection" refers to any state in at least one cell of an organism (i.e., a subject) is infected by an infectious agent (e.g., a subject has an intracellular pathogen infection, e.g., a chronic intracellular pathogen infection). As used herein, the term "infectious agent" refers to a foreign biological entity (i.e. a pathogen) that induces increased CD47 expression in at least one cell of the infected organism. For example, infectious agents include, but are not limited to bacteria, viruses, protozoans, and fungi. Intracellular pathogens are of particular interest. Infectious diseases are disorders caused by infectious agents. Some infectious agents cause no recognizable symptoms or disease under certain conditions, but have the potential to cause symptoms or disease under changed conditions. The subject methods can be used in the treatment of chronic pathogen infections, for example including but not limited to viral infections, e.g. retrovirus, lentivirus, hepadna virus, herpes viruses, pox viruses, human papilloma viruses, etc.; intracellular bacterial infections, e.g. *Mycobacterium, Chlamydophila, Ehrlichia, Rickettsia, Brucella, Legionella, Francisella, Listeria, Coxiella, Neisseria, Salmonella, Yersinia sp, Helicobacter pylori* etc.; and intracellular protozoan pathogens, e.g. *Plasmodium* sp, *Trypanosoma* sp., *Giardia* sp., *Toxoplasma* sp., *Leishmania* sp., etc.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

The term "sample" with respect to a patient encompasses blood and other liquid samples of biological origin, solid tissue samples such as a biopsy specimen or tissue cultures or cells derived or isolated therefrom and the progeny thereof. The definition also includes samples that have been manipulated in any way after their procurement, such as by treatment with reagents; washed; or enrichment for certain cell populations, such as cancer cells. The definition also includes samples that have been enriched for particular types of molecules, e.g., nucleic acids, polypeptides, etc.

The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample comprising target cells or normal control cells or suspected of comprising such cells or biological fluids derived therefrom (e.g., cancerous cell, infected cell, etc.), e.g., a sample comprising polynucleotides and/or polypeptides that is obtained from such cells (e.g., a cell lysate or other cell extract comprising polynucleotides and/or polypeptides). A biological sample comprising an inflicted cell from a patient can also include non-inflicted cells.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules without known antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

The term T cells refers to mammalian immune effector cells that may be characterized by expression of CD3 and/or T cell antigen receptor, which cells may respond to the phAPC by priming for an effector cell response appropriate for the subset of T cells. In some embodiments the T cells are cytotoxic T cells, (CTL), which may be characterized as CD8+ T cells.

In some embodiments the T cells are contacted with phAPC in vivo, i.e. where an effective dose of the phAPC are injected into the recipient and allowed to interact with T cells in their native environment, e.g. in lymph nodes, etc. In other embodiments the contacting is performed in vitro.

T cells collected from the subject may be separated from a mixture of cells by techniques that enrich for desired cells. An appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, eg. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the selected cells. The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

The collected and optionally enriched cell population may be used immediately, or may be frozen at liquid nitrogen temperatures and stored, being thawed and capable of being reused. The cells will usually be stored in 10% DMSO, 50% FCS, 40% RPMI 1640 medium.

The T cells may be reinfused to the subject in any physiologically acceptable medium, normally intravascularly, although they may also be introduced into any other convenient site, where the cells may find an appropriate site for growth. Usually, at least $1\times10^6$ cells/kg will be administered, at least $1\times10^7$ cells/kg, at least $1\times10^8$ cells/kg, at least $1\times10^9$ cells/kg, at least $1\times10^{10}$ cells/kg, or more, usually being limited by the number of T cells that are obtained during collection.

Methods

Methods are provided for enhancing T cell mediated immune response to an antigen, particularly a particulate antigen and more particularly a target cell. The subject methods include a step of obtaining phagocytic antigen presenting cells, which may be isolated from a biological sample, or may be derived in vitro from a source of progenitor cells, including without limitation monocytes from blood or bone marrow; followed by a step of contacting the phAPC with a particulate antigen in the presence of an effective dose of an anti-CD47 agent. The contacting may be performed in any suitable culture medium. The phAPC phagocytoses the particulate antigen, generally from about one to about 4 hours is sufficient for phagocytosis. The loaded phAPC processes proteins from the target cell and presents them on the cell surface. The loaded phAPC is contacted with a population of T cells in vivo or in vitro.

Where the contacting is performed in vitro, an isolated T cell population is added to the phAPC in a dose and for a period of time sufficient to prime the T cells. Generally the ratio of T cell to APC is anywhere from 1:10 to 10:1, and is not critical so long as the number of phAPC is not limiting. Any suitable culture medium may be used. A period of from up to 8 days, up to 10 days, up to 12 days, up to 14 days may be sufficient (see, for example, Dudley et al, JCO 2005; 23(10):2346-2357). The T cells thus primed may be used for any desired purpose, including experimental purposes relating to determination of antigen specificity, cytokine profiling, and the like, and for delivery in vivo.

Where the contacting is performed in vivo, an effective dose of loaded phAPC are administered to the recipient. Dosage and frequency may vary depending on the anti-CD47 agent; mode of administration; nature of the antigen; and the like. It will be understood by one of skill in the art that such guidelines will be adjusted for the individual circumstances. The dosage may also be varied for localized administration, e.g. intranasal, inhalation, etc., or for systemic administration, e.g. i.m., i.p., i.v., and the like. Generally at least about $10^4$ phAPC/kg are administered, at least about $10^5$ phAPC/kg; at least about $10^6$ phAPC/kg, at least about $10^7$ phAPC/kg, or more.

The enhanced immune response may be manifest as an increase in the cytolytic response of T cells towards the target cells present in the recipient, e.g. towards elimination of tumor cells, infected cells; combining the primed T cells with HLA-matched targets to test for cytotoxic activity; determination of intracellular cytokine analysis; and the like.

Kits

Also provided are kits for use in the methods. The subject kits include an anti-CD47 agent, for example in a dosage form (e.g., a priming dosage form). In some embodiments, an anti-CD47 agent is provided in a dosage form (e.g., a therapeutically effective dosage form), in liquid or solid form in any convenient packaging (e.g., stick pack, dose pack, etc.). Reagents for the selection or in vitro derivation of phAPC may also be provided, e.g. M-CSF, IL-4, tissue culture reagents; particulate antigen, and the like.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Utility.

The subject methods and kits can be used to enhance a T cell mediated immune response. In some embodiments the immune response is directed towards a condition where the target cells (e.g., cancer cells, infected cells, etc.) exhibit an increased expression of CD47 relative to normal cells of the same type. The anti-CD47 agent inhibits the interaction between SIRPα (on the phAPC) and CD47 on an target cell (e.g., particulate antigen including a cancer cell, an infected cell, etc.), thereby increasing phagocytosis of the target cell and presentation of antigens from the target cell.

In some embodiments the condition is a chronic infection, i.e. an infection that is not cleared by the host immune system within a period of up to 1 week, 2 weeks, etc. In some cases, chronic infections involve integration of pathogen genetic elements into the host genome, e.g. retroviruses, lentiviruses, Hepatitis B virus, etc. In other cases, chronic infections, for example certain intracellular bacteria or protozoan pathogens, result from a pathogen cell residing within a host cell. Additionally, in some embodiments, the infection is in a latent stage, as with herpes viruses or human papilloma viruses.

Viral pathogens of interest include without limitation, retroviral and lentiviral pathogens, e.g. HIV-1; HIV-2, HTLV, FIV, SIV, etc. Hepatitis B virus, etc. Microbes of interest, but not limited to the following, include: *Yersinia* sp., e.g. *Y. pestis, Y. pseudotuberculosis, Y. enterocolitica; Franciscella* sp.; *Pasteurella* sp.; *Vibrio* sp., e.g. *V. cholerae, V. parahemolyticus; Legionella* sp., e.g. *L. pneumophila; Listeria* sp., e.g. *L. monocytogenes; Mycoplasma* sp., e.g. *M. hominis, M. pneumoniae; Mycobacterium* sp., e.g. *M. tuberculosis, M. leprae; Rickettsia* sp., e.g. *R. rickettsii, R. typhi; Chlamydia* sp., e.g. *C. trachomatis, C. pneumoniae, C. psittaci; Helicobacter* sp., e.g. *H. pylori*, etc. Also included are intracellular protozoan pathogens, e.g. *Plasmodium* sp, *Trypanosoma* sp., *Giardia* sp., *Toxoplasma* sp., *Leishmania* sp., etc.

An infection treated with the methods of the invention generally involves a pathogen with at least a portion of its life-cycle within a host cell, i.e. an intracellular phase. The methods of the invention provide for a more effective killing of infected cells by the T effector cells of the host organism, relative to removal in the absence of treatment, and thus are directed to the intracellular phase of the pathogen life cycle. The methods may further include monitoring the patient for efficacy of treatment. Monitoring may measure clinical indicia of infection, e.g. fever, white blood cell count, etc., and/or direct monitoring for presence of the pathogen.

Treatment may be combined with other active agents. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; chloramphenical; metronidazole; spectinomycin; trimethoprim; vancomycin; etc. Cytokines may also be included, e.g. interferon γ, tumor necrosis factor α, interleukin 12, etc. Antiviral agents, e.g. acyclovir, gancyclovir, etc., may also be used in treatment.

In some embodiments the condition is cancer. As noted above, any cancer in which a cancerous cell expresses an increased level of CD47 relative to a non-cancerous cell of the same type can be treated with the subject methods.

The term "cancer", as used herein, refers to a variety of conditions caused by the abnormal, uncontrolled growth of cells. Cells capable of causing cancer, referred to as "cancer cells", possess characteristic properties such as uncontrolled proliferation, immortality, metastatic potential, rapid growth and proliferation rate, and/or certain typical morphological features. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer, and detecting a genotype indicative of a cancer. However, a negative result in one or more of the above detection methods does not necessarily indicate the absence of cancer, e.g., a patient who has exhibited a complete response to a cancer treatment may still have a cancer, as evidenced by a subsequent relapse.

The term "cancer" as used herein includes carcinomas, (e.g., carcinoma in situ, invasive carcinoma, metastatic carcinoma) and pre-malignant conditions, i.e. neomorphic changes independent of their histological origin. The term "cancer" is not limited to any stage, grade, histomorphological feature, invasiveness, aggressiveness or malignancy of an affected tissue or cell aggregation. In particular stage 0 cancer, stage I cancer, stage II cancer, stage III cancer, stage IV cancer, grade I cancer, grade II cancer, grade III cancer, malignant cancer and primary carcinomas are included.

Cancers and cancer cells that can be treated include, but are not limited to, hematological cancers, including leukemia, lymphoma and myeloma, and solid cancers, including for example tumors of the brain (glioblastomas, medulloblastoma, astrocytoma, oligodendroglioma, ependymomas), carcinomas, e.g. carcinoma of the lung, liver, thyroid, bone, adrenal, spleen, kidney, lymph node, small intestine, pancreas, colon, stomach, breast, endometrium, prostate, testicle, ovary, skin, head and neck, and esophagus.

In an embodiment, the cancer is a hematological cancer. In an embodiment, the hematological cancer is a leukemia. In another embodiment, the hematological cancer is a myeloma. In an embodiment, the hematological cancer is a lymphoma.

In an embodiment, the leukemia is selected from acute myeloid leukemia (AML), acute lymphocytic leukemia (ALL), chronic lymphocytic leukemia (CLL) and chronic myelogenous leukemia (CML). In an embodiment, the leukemia is AML. In an embodiment, the leukemia is ALL. In an embodiment, the leukemia is CLL. In a further embodiment, the leukemia is CML. In an embodiment, the cancer cell is a leukemic cell, for example, but not limited to, an AML cell, an ALL cell, a CLL cell or a CML cell.

Suitable cancers include, without limitation, leukemia; acute myeloid leukemia (AML); acute lymphoblastic leukemia (ALL); metastasis; minimal residual disease; solid tumor cancers, e.g., breast, bladder, colon, ovarian, glioblastoma, leiomyosarcoma, and head & neck squamous cell carcinomas; etc. For examples, see: (i) Willingham et al., Proc Natl Acad Sci USA. 2012 Apr. 24; 109(17):6662-7: "The CD47-signal regulatory protein alpha (SIRPα) interaction is a therapeutic target for human solid tumors"; (ii) Edris et al., Proc Natl Acad Sci USA. 2012 Apr. 24; 109(17):6656-61: "Antibody therapy targeting the CD47 protein is effective in a model of aggressive metastatic leiomyosarcoma"; and (iii) US patent application 20110014119; all of which are herein incorporated in their entirety.

Pharmaceutical Compositions.

Loaded phAPC or primed T cells can be provided in pharmaceutical compositions suitable for therapeutic use, e.g. for human treatment. Therapeutic formulations comprising such cells can be frozen, or prepared for administration with physiologically acceptable carriers, excipients or stabilizers (Remington's Pharmaceutical Sciences 16th edition, Osol, A. Ed. (1980)), in the form of aqueous solutions. The cells will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The cells can be administered by any suitable means, usually parenteral. Parenteral infusions include intramuscular, intravenous (bollus or slow drip), intraarterial, intraperitoneal, intrathecal or subcutaneous administration.

The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions can also include large, slowly metabolized macromolecules such as proteins, polysaccharides such as chitosan, polylactic acids, polyglycolic acids and copolymers (such as latex functionalized Sepharose™ agarose, cellulose, and the like), polymeric amino acids, amino acid copolymers, and lipid aggregates (such as oil droplets or liposomes).

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLES

Anti-CD47 Antibody-Mediated Phagocytosis of Cancer by Macrophages Primes an Effective Anti-Tumor T Cell Response Mobilization of the T cell response against cancer has the potential to achieve long-lasting cures. However, it is not known how to optimally harness antigen presenting cells to achieve an effective anti-tumor T cell response. In this study, we show that anti-CD47 antibody-mediated phagocytosis of cancer by macrophages can initiate an anti-tumor T cell immune response. Using the ovalbumin model antigen system, anti-CD47 antibody-mediated phagocytosis of cancer cells by macrophages resulted in increased priming of OT-I T cells (CD8$^+$), but did not prime OT-II T cells (CD4$^+$). The CD4+ T cell response was characterized by a reduction in Foxp3$^+$ regulatory T cells. Macrophages following anti-CD47-mediated phagocytosis primed CD8$^+$ T cells to exhibit cytotoxic function in vivo. This response protected animals from tumor challenge. We conclude that anti-CD47 antibody treatment not only enables macrophage phagocytosis of cancer, but can also initiate an anti-tumor cytotoxic T cell immune response.

In this study, it was tested whether anti-CD47 antibody-mediated phagocytosis of cancer cells can facilitate an anti-tumor T cell immune response.

Macrophages Phagocytose Cancer Cells in the Presence of Anti-CD47 B6H12 Antibody.

Figure 7A:
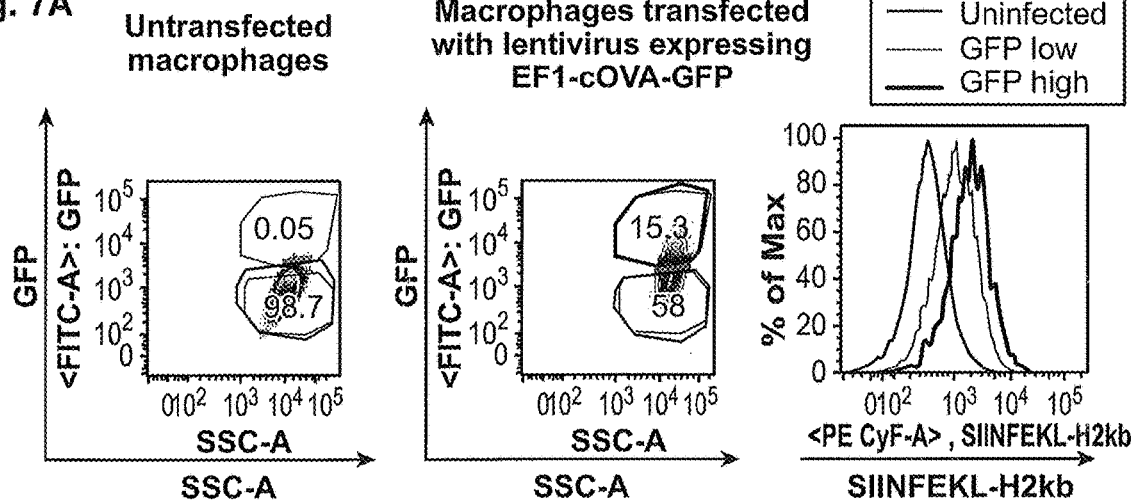
FIG. 7A-7C: Generation of DLD1-cOVA-GFP colon cancer cell line.
Figure 7B:
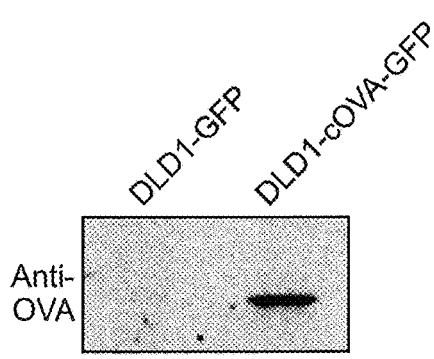
Figure 7C:
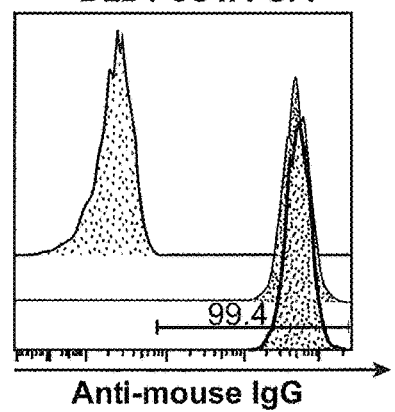
Figure 8A:
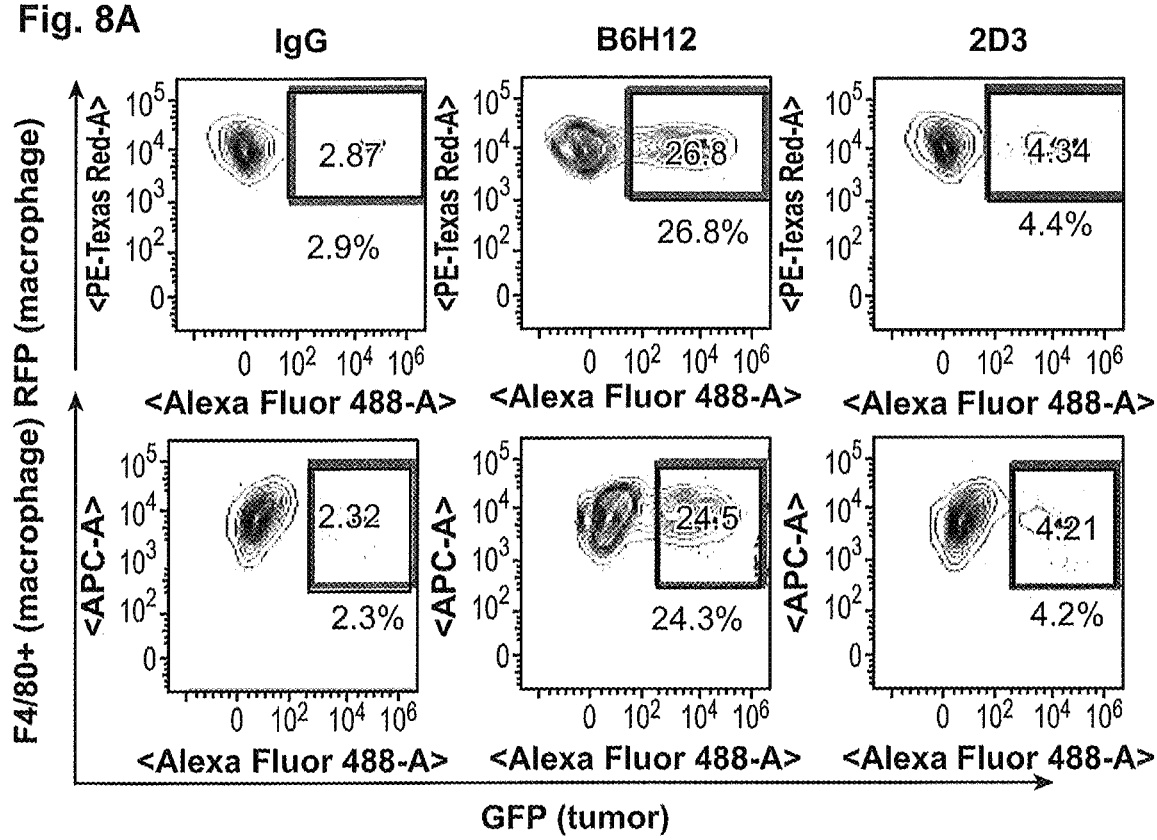
FIG. 8A-8B: Anti-CD47 B6H12 mAb mediates phagocytosis of cancer by macrophages.
Figure 8B:
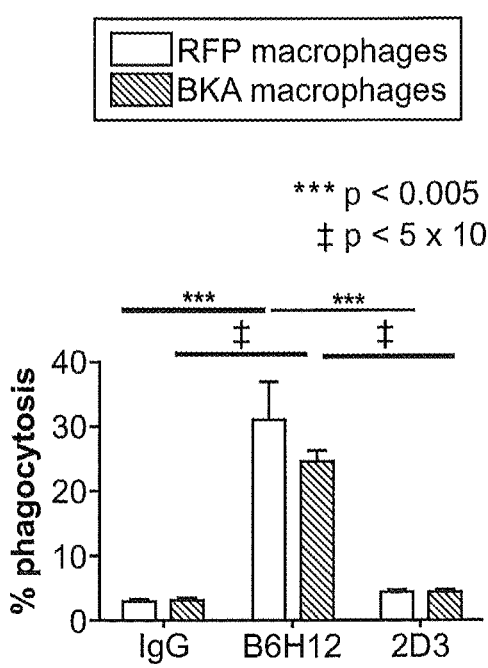
Figure 8B:
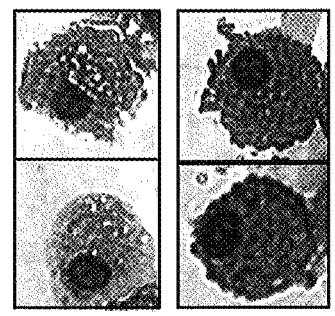
Figure 8B:
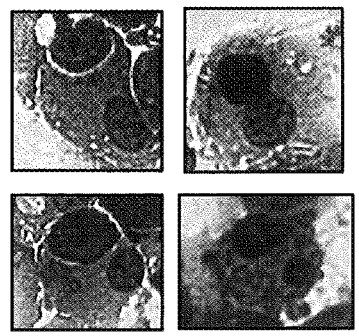
Figure 9:
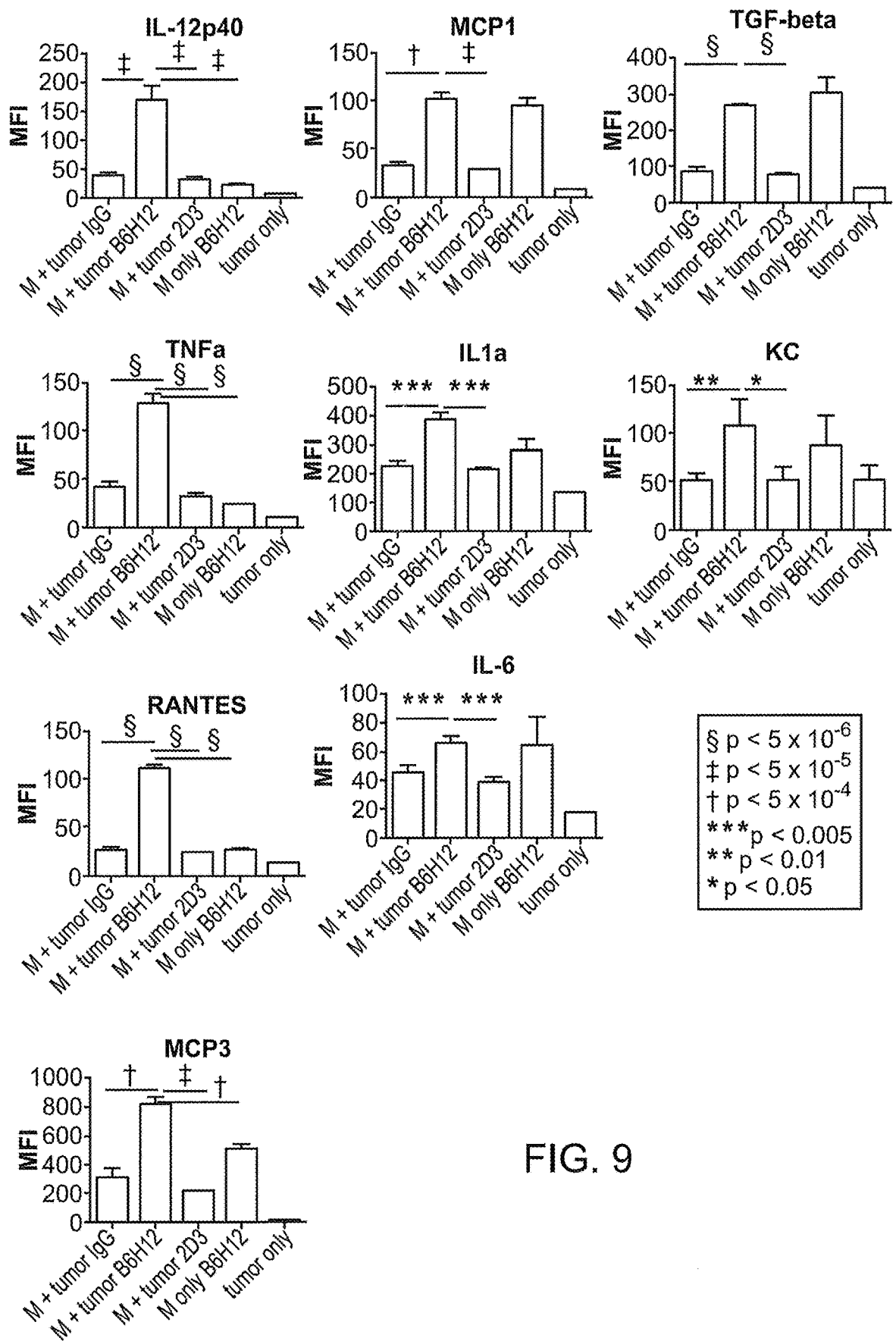
FIG. 9: Following anti-CD47 B6H12 mediated phagocytosis, macrophages secrete increased amounts of pro-inflammatory cytokines. $RFP^+$ macrophages were co-cultured with DLD1-cOVA-GFP cancer cells (designated $M^+$ tumor) in the presence of IgG or anti-CD47 mAbs B6H12 (blocking) or 2D3 (non-blocking). In addition, $RFP^+$ macrophages were also cultured alone in the context of B6H12 mAb (M only B6H12) to distinguish between cytokines released due to macrophage phagocytosis versus cytokine released by mAb stimulation of the macrophage. Culture supernatants were harvested for analysis of cytokine levels by luminex assay.

To follow the immune response to a model tumor antigen, the human colon cancer cell line DLD1 was transfected with a lentiviral vector expressing cytoplasmic ovalbumin and GFP (DLD1-cOVA-GFP) (FIG. 7). DLD1-cOVA-GFP cancer cells express CD47 and can be recognized by both anti-human CD47 mAbs, clones B6H12 and 2D3 (FIG. 7). Anti-CD47 B6H12 antibody blocks the interaction between CD47 and SIRPα, whereas anti-CD47 2D3 antibody binds CD47 but does not block its interaction with SIRPα. Macrophages phagocytose DLD1-cOVA-GFP cancer cells in the presence of anti-CD47 B6H12, but not anti-CD47 2D3 mAbs, confirming that anti-CD47 mediated phagocytosis is dependent on blockade of CD47/SIRPα interactions (FIG. 1; FIG. 8). Anti-CD47 B6H12-mediated phagocytosis of cancer cells leads to macrophage release of proinflammatory cytokines. For example, IL-12p40, TNFα, RANTES, and MCP-3 cytokine levels increase following B6H12-mediated phagocytosis (FIG. 9). The ability of the APCs, macrophages and dendritic cells, were tested for phagocytic activity in response to anti-CD47 mAbs. Compared to macrophages, dendritic cells are not as efficient at phagocytosing DLD1-cOVA-GFP cancer cells in the presence of anti-CD47 B6H12 mAb (FIG. 1). Consistent with this result, SIRP□, the ligand for CD47, is expressed at high levels on macrophages but at lower levels on dendritic cells (FIG. 10).

Macrophages Prime OT-1 (CD8$^+$) T Cells Following Phagocytosis of Cancer Cells by Anti-Cd47 B6H12 Antibody.

Figure 2A:
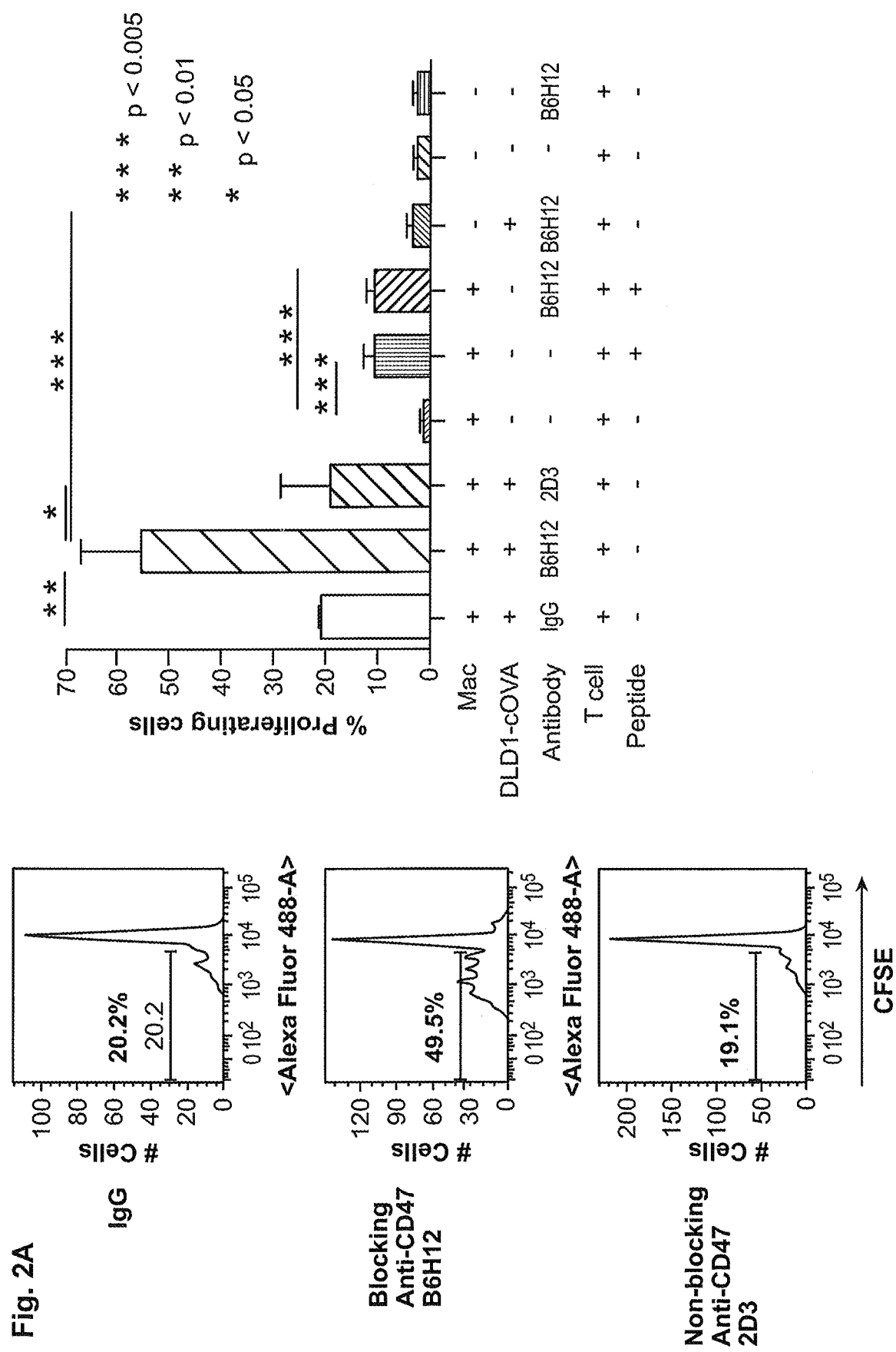
FIG. 2A-2B. Macrophages effectively prime CD8$^+$ T cells to proliferate following phagocytosis of cancer cells by anti-CD47 B6H12 antibody.
Figure 2B:
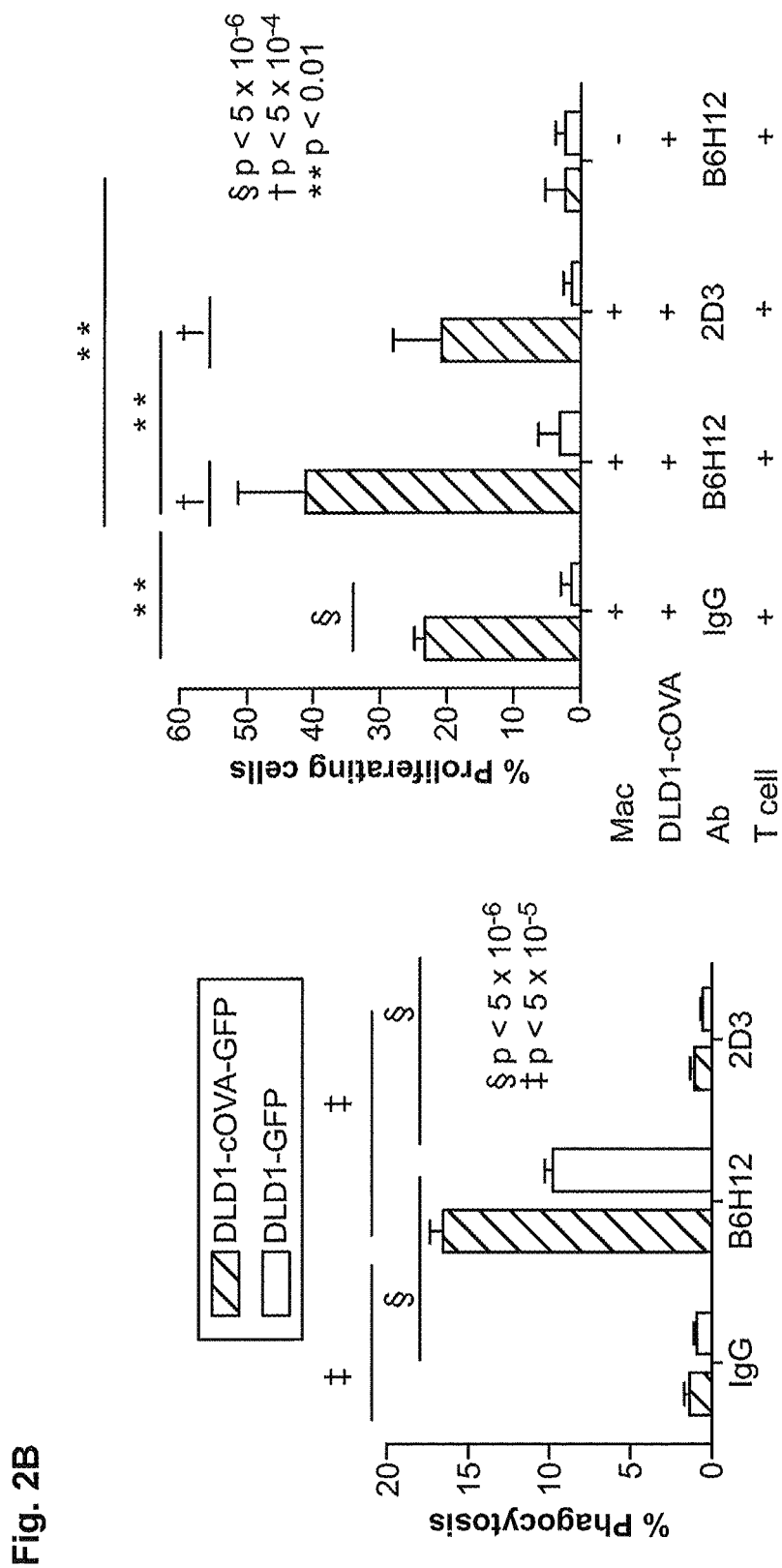

To assess antigen presentation to CD8$^+$ T cells following anti-CD47-mediated phagocytosis by macrophages, a CFSE dilution assay was used to measure the proliferative response of ovalbumin-specific CD8$^+$ T cells (OT-1). RFP$^+$ macrophages were co-cultured with DLD1-cOVA-GFP cancer cells in the presence of IgG, blocking anti-CD47 B6H12, or non-blocking anti-CD47 2D3 antibodies. Lymph nodes were harvested from OT-1 (CD8$^+$) transgenic mice, labeled with CFSE (0.5 μM), and CD8$^+$ cells enriched by magnetic separation. On day 3, the percentage of proliferating OT-I T cells was quantified based on the percent of cells that had diluted the CFSE dye (CFSE low). The percentage of proliferating OT-I T cells increased in the presence of macrophages that had phagocytosed cancer cells following anti-CD47 B6H12 mAb treatment (FIG. 2A). To verify that the proliferative response of OT-I T cells was an antigen-specific response, macrophages were allowed to phagocytose DLD1-cOVAGFP versus DLD1-GFP cancer cells (the latter not expressing ovalbumin) in the presence of blocking anti-CD47 B6H12 mAb prior to addition of CFSE-labeled OT-I T cells. Increased OTI T cell proliferation was only observed following anti-CD47-mediated phagocytosis of DLD1-cOVA-GFP cancer cells, but not DLD1-GFP cancer cells, indicating an antigen-specific effect (FIG. 2B).

Macrophages do not Prime OT-II (CD4$^+$) T Cells Following Phagocytosis of Cancer Cells by Anti-CD47 B6H12 Antibody.

To assess activation of CD4$^+$ T cells following anti-CD47-mediated phagocytosis by macrophages, a CFSE dilution assay was used to measure the proliferative response of ovalbumin specific CD4$^+$ T cells (OT-II). Macrophages were allowed to phagocytose DLD1-cOVA-GFP cancer cells in the presence of anti-CD47 B6H12 mAb, and CFSE-labeled OT-II (CD4$^+$) T cells were added to cultures. Interestingly, the percentage of proliferating OT-II T cells diminished in the presence of macrophages that had phagocytosed cancer cells in the presence of blocking anti-CD47 B6H12 mAb compared to baseline levels (FIG. 3A).

Figure 3B:
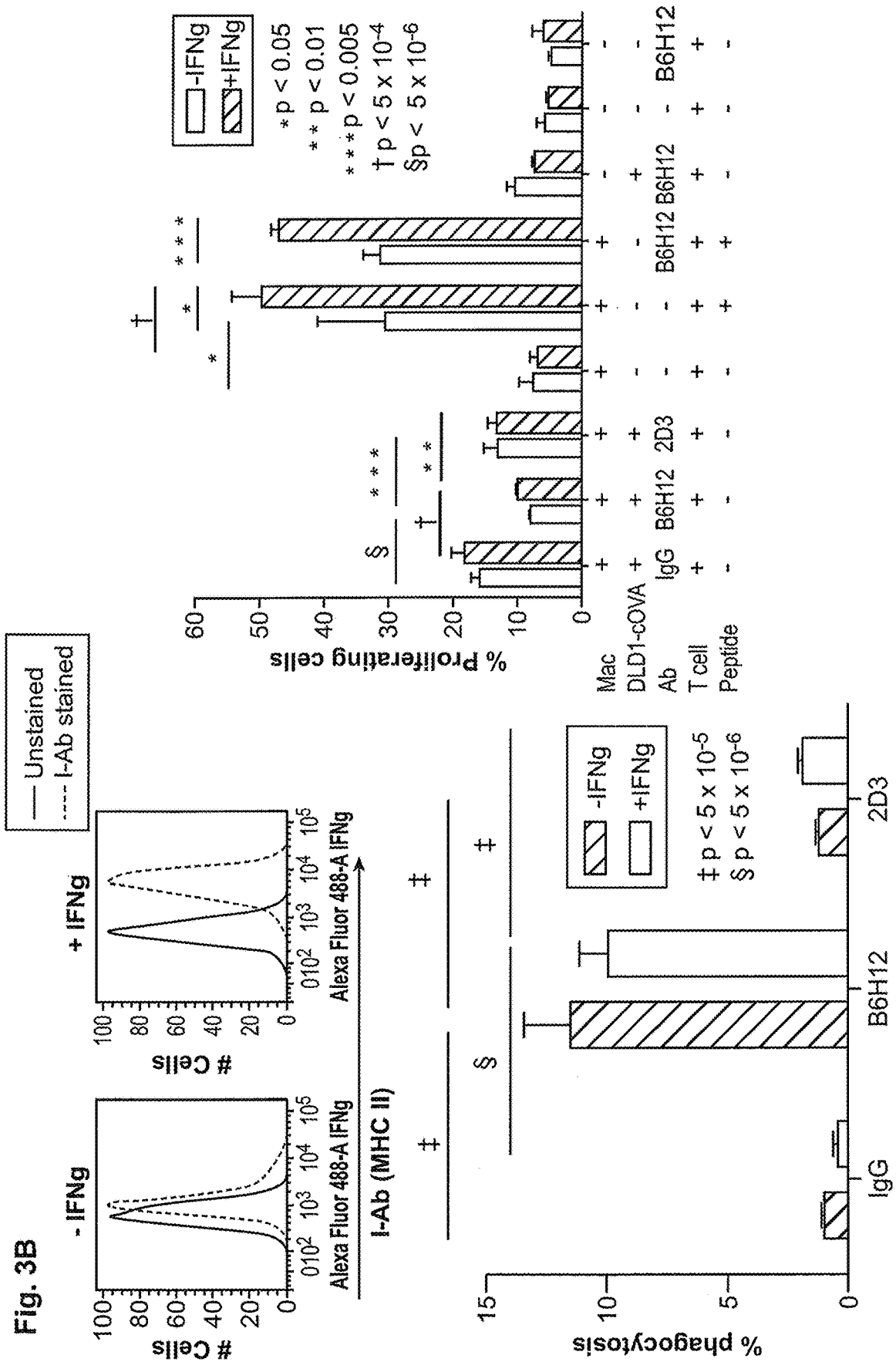
Figure 11A:
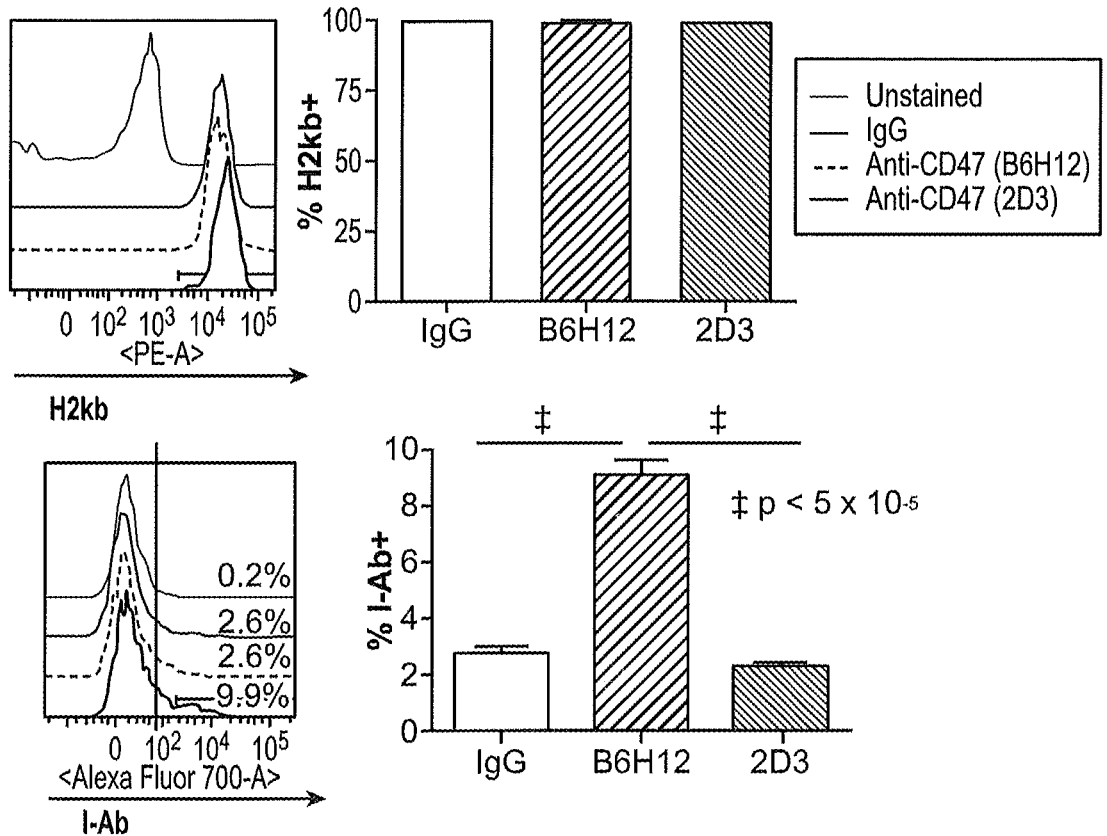
FIG. 11A-11B. Macrophages upregulate MHC II and costimulatory molecule CD86 following phagocytosis of tumors by anti-CD47 antibody.
Figure 11B:
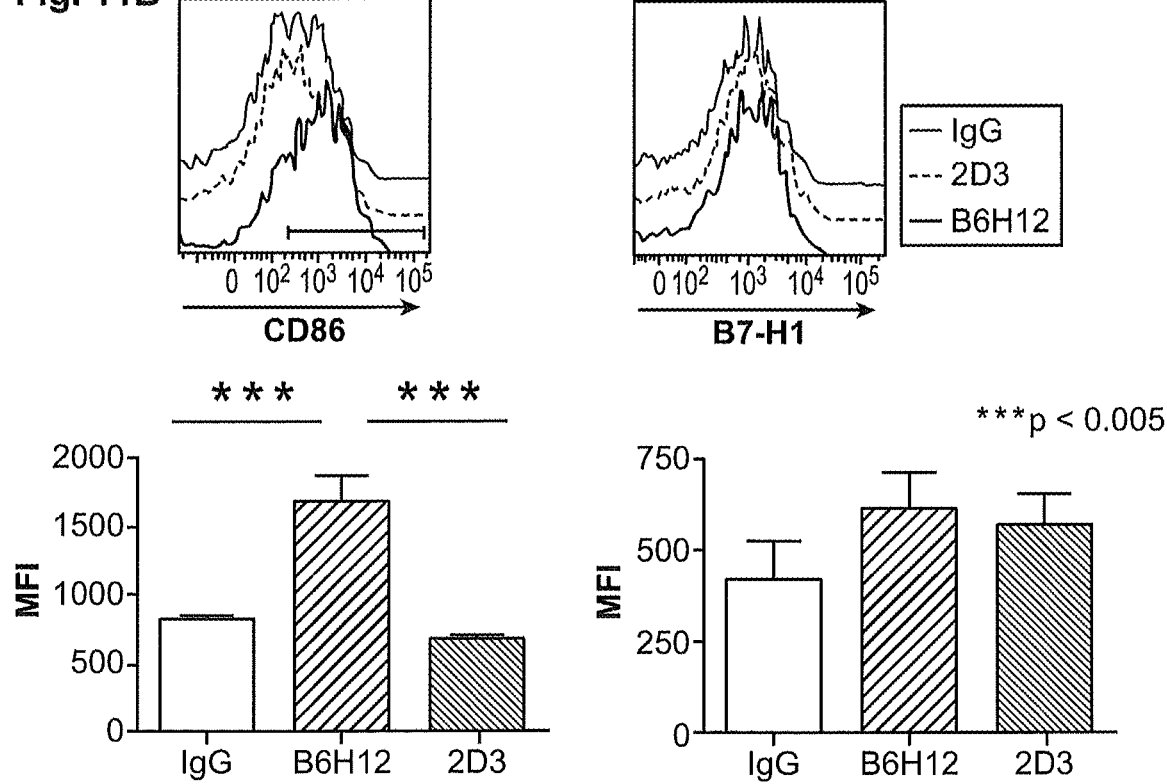

Because this result might be due limited availability of MHC II (I-Ab$^+$), we measured the percentage of macrophages expressing MHC II on the cell surface after anti-CD47 B6H12-mediated phagocytosis. Interestingly, the percentage of I-Ab$^+$ macrophages increased following anti-CD47 B6H12-mediated phagocytosis of cancer cells, despite the decrease in CD4$^+$ T cell activation (FIG. 11). To further determine whether the availability of MHC II on macrophages was limiting the proliferative response to CD4$^+$ T cells, IFN-γ was used to upregulate surface MHC II levels on macrophages for evaluation in phagocytosis and antigen presentation assays. IFN-γ stimulated macrophages efficiently phagocytosed cancer in the presence of anti-CD47 B6H12 mAb, and the OT-II CD4$^+$ T cell response was still diminished compared to baseline (FIG. 3B).

A Reduction in Foxp3$^+$ Regulatory T Cells Occurs after CD4$^+$ T Cells Encounter Macrophages Undergoing Anti-CD47 B6H12-Mediated Phagocytosis of Cancer.

Figure 4:
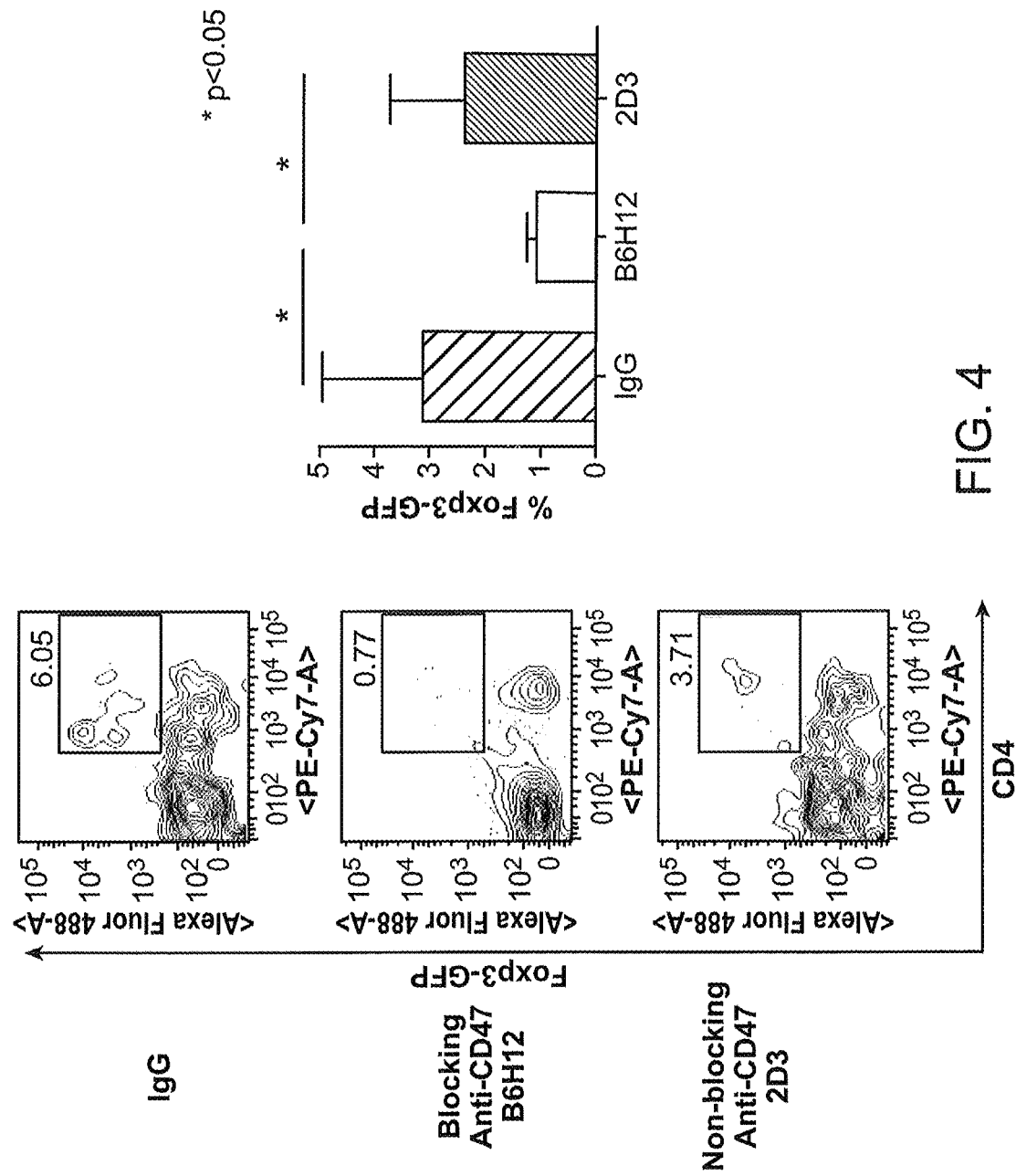
FIG. 4. A reduction in Foxp3$^+$ regulatory T cells occurs following anti-CD47 B6H12-mediated phagocytosis of cancer by macrophages. RFP$^+$ macrophages were co-cultured with DLD1-cOVA-GFP cancer cells in the presence of IgG or anti-CD47 mAbs B6H12 (blocking) or 2D3 (nonblocking). The following day, CD4$^+$ T cells were magnetically enriched from OT-II/Foxp3-GFP$^+$ transgenic mice and added to cultures. On day 4, % CD4$^+$ Foxp3-GFP$^+$ cells were quantified.
Figure 12A:
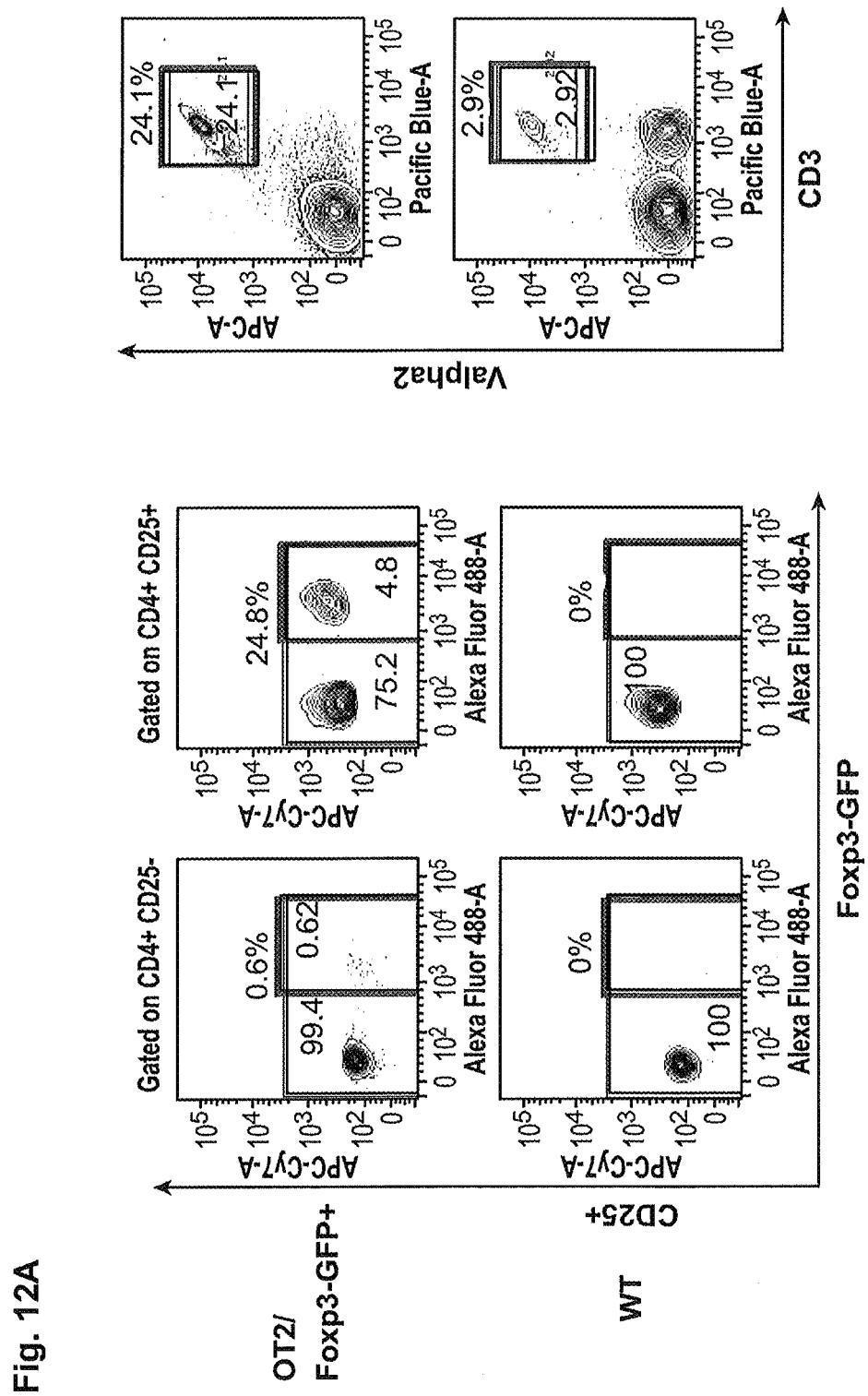
FIG. 12A-12B. Validation of OT-II/Foxp3-GFP double transgenic mice.
Figure 12B:
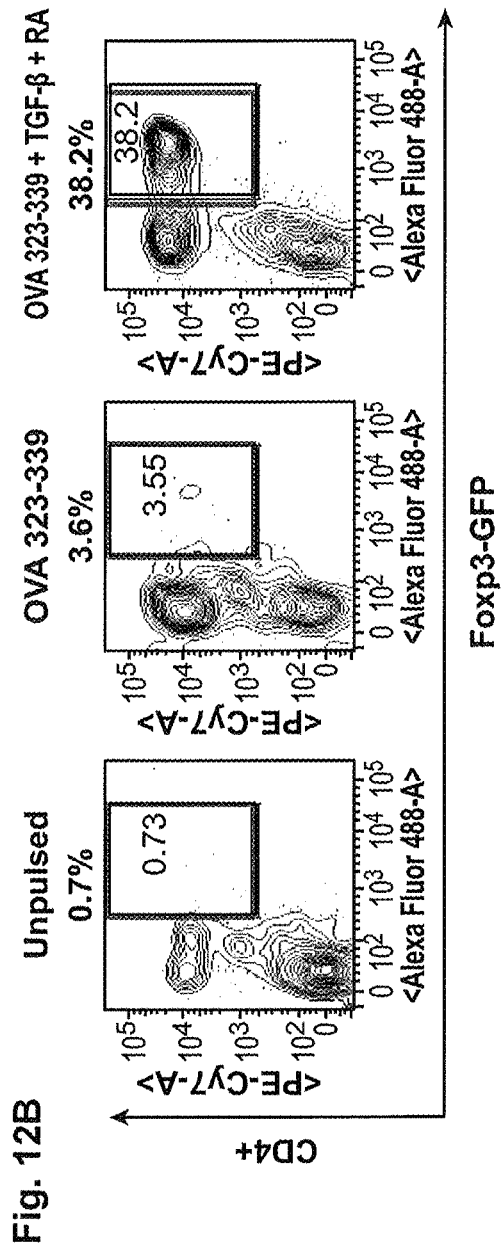
Figure 12B:
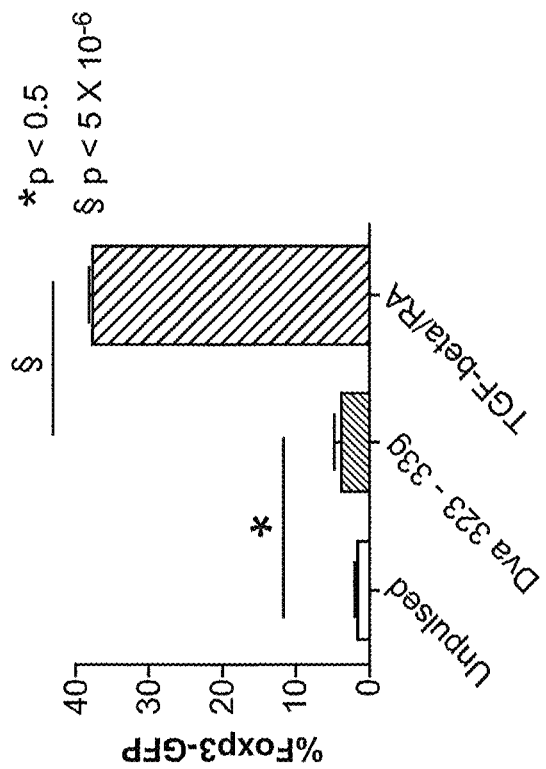
Figure 13:
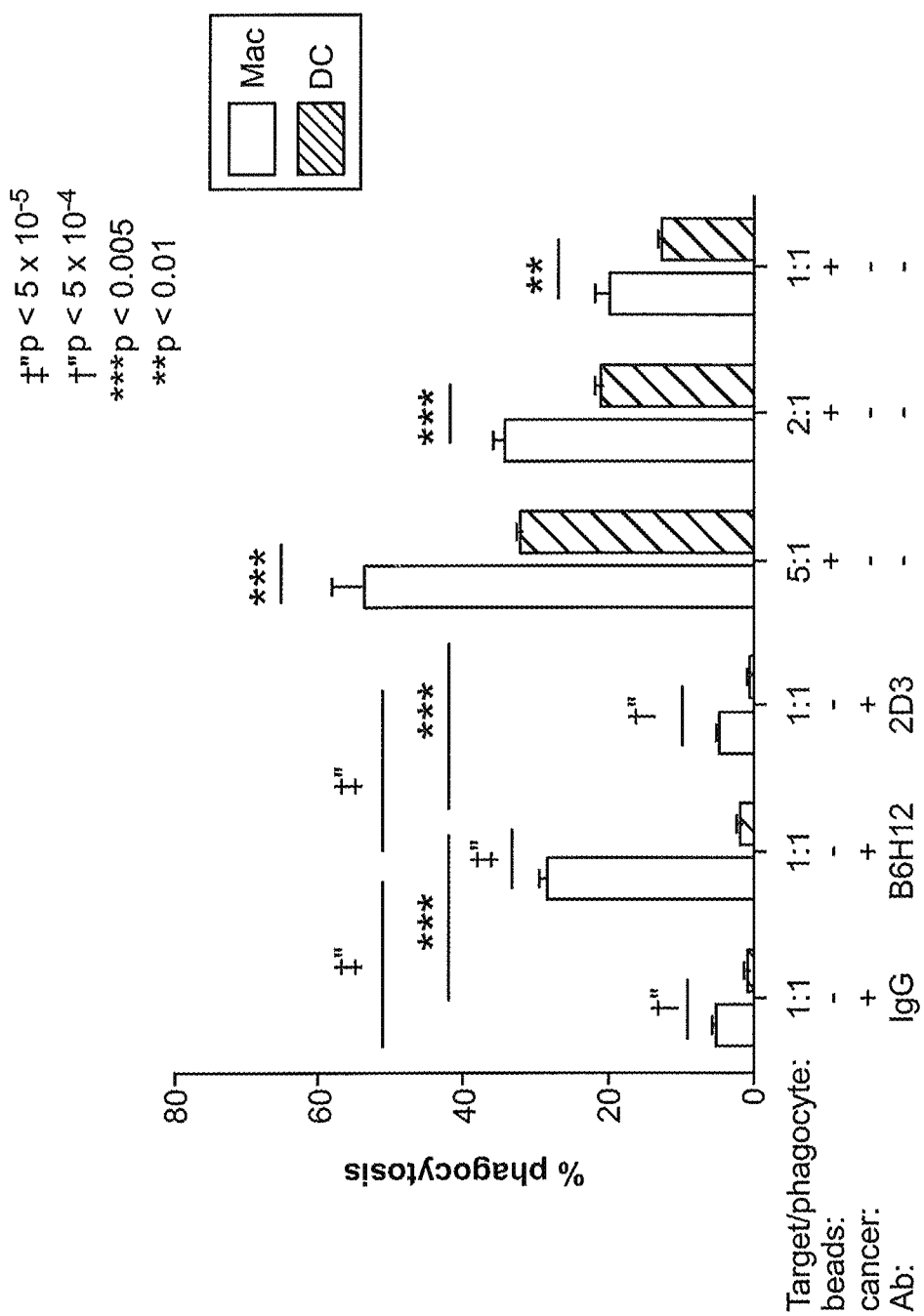
FIG. 13. Macrophages are more efficient at phagocytosing targets compared to dendritic cells. Macrophages and dendritic cells were compared side-by-side for their ability to phagocytose targets. Anti-CD47-mediated phagocytosis of DLD1-cOVA-GFP colon cancer cells was tested along with ovalbumin-coated yellow-green latex beads.
Figure 14:
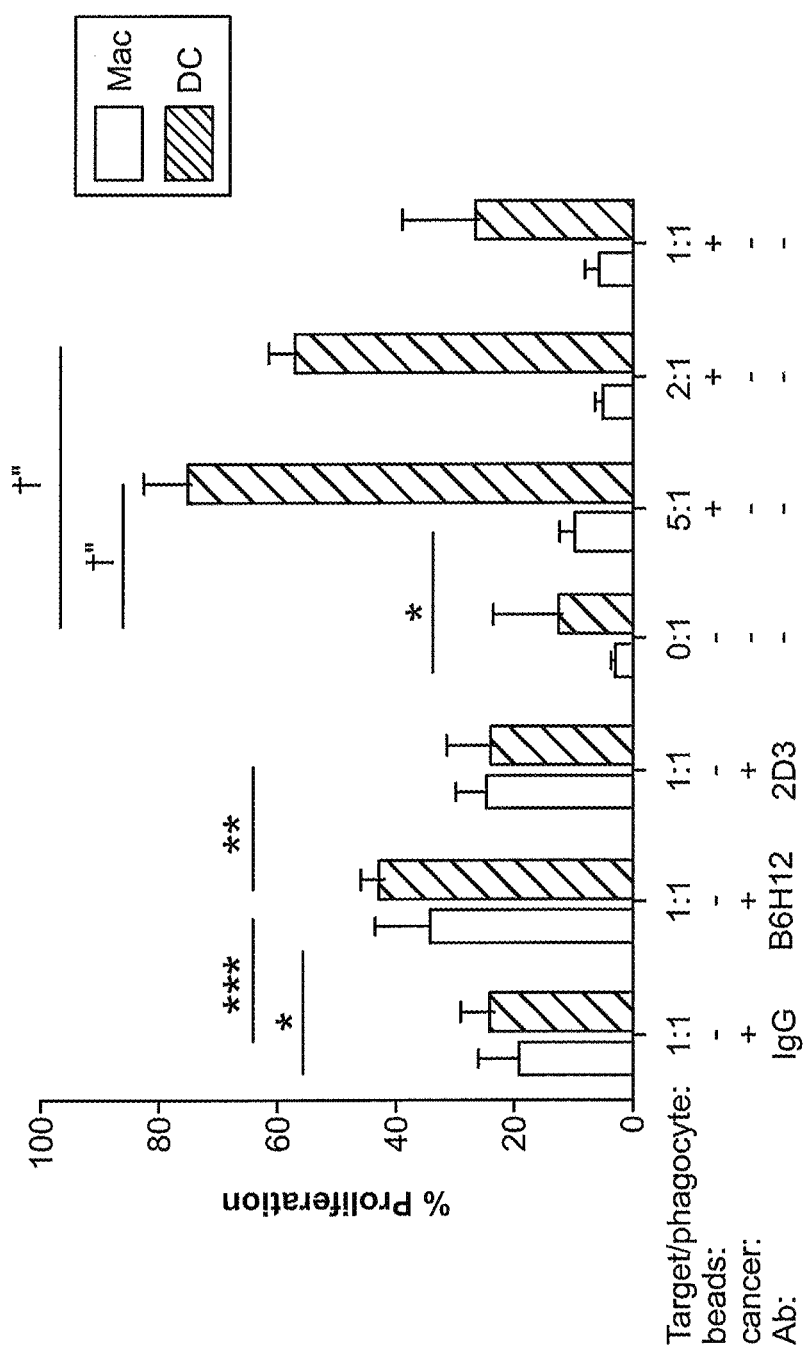
FIG. 14. Following anti-CD47-mediated phagocytosis, macrophages and dendritic cells prime a CD8+ T cell response. Macrophages and dendritic cells were co-cultured with targets (DLD1-cOVA-GFP colon cancer cells or ovalbumin-coated latex beads), and priming of CD8+ T cells was measured by % proliferation of OT-I (CD8+) T cells.
Figure 15:
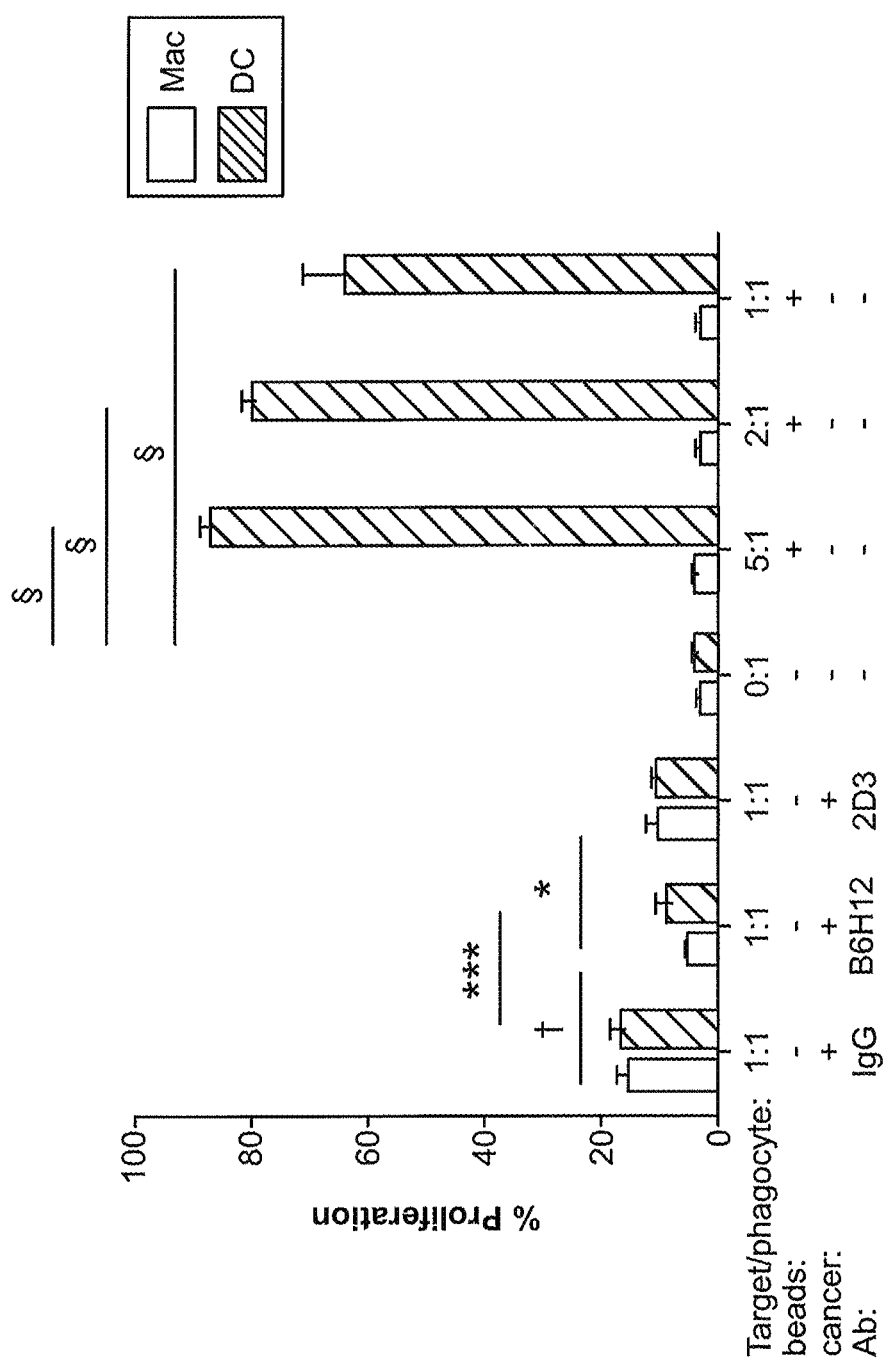
FIG. 15. Following anti-CD47-mediated phagocytosis, macrophages and dendritic cells do not prime a CD4+ T cell response. Macrophages and dendritic cells were co-cultured with targets (DLD1-cOVA-GFP colon cancer cells or ovalbumin-coated latex beads), and priming of CD4+ T cells was measured by % proliferation of OT-II (CD4+) T cells.
Figure 16:
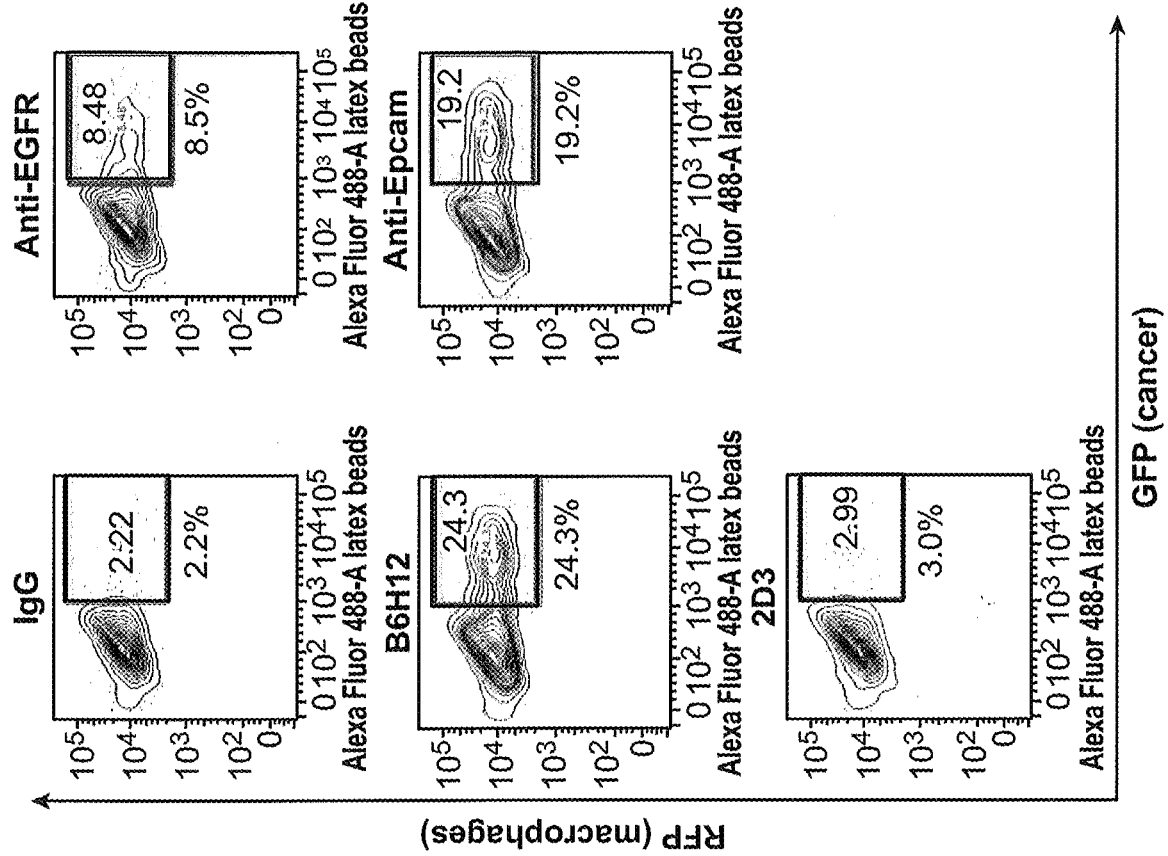
FIG. 16. Anti-CD47, cetuximab (anti-EGFR), and anti-Epcam antibodies induce phagocytosis of cancer cells by in vitro by macrophages. RFP+ macrophages were co-cultured with DLD1-cOVA-GFP cancer cells in the presence of IgG, anti-CD47 B6H12 (blocking), or anti-CD47 2D3 (non-blocking), anti-EGFR, and anti-Epcam mAbs.
Figure 16:
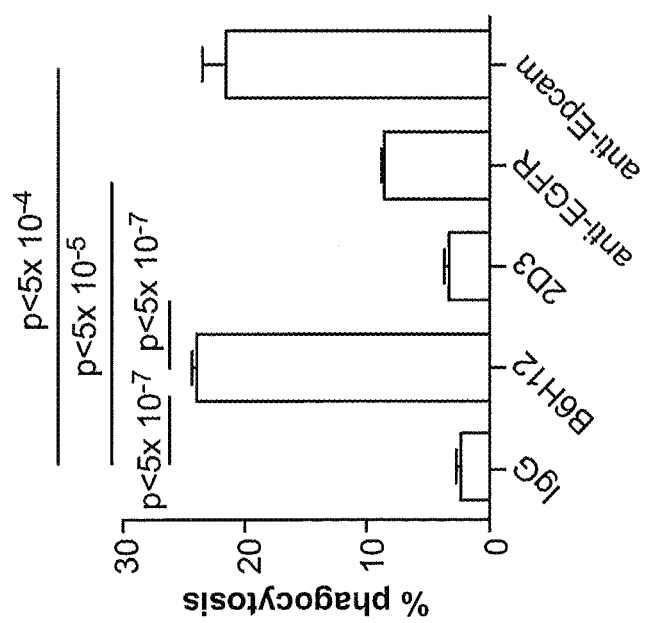
Figure 17:
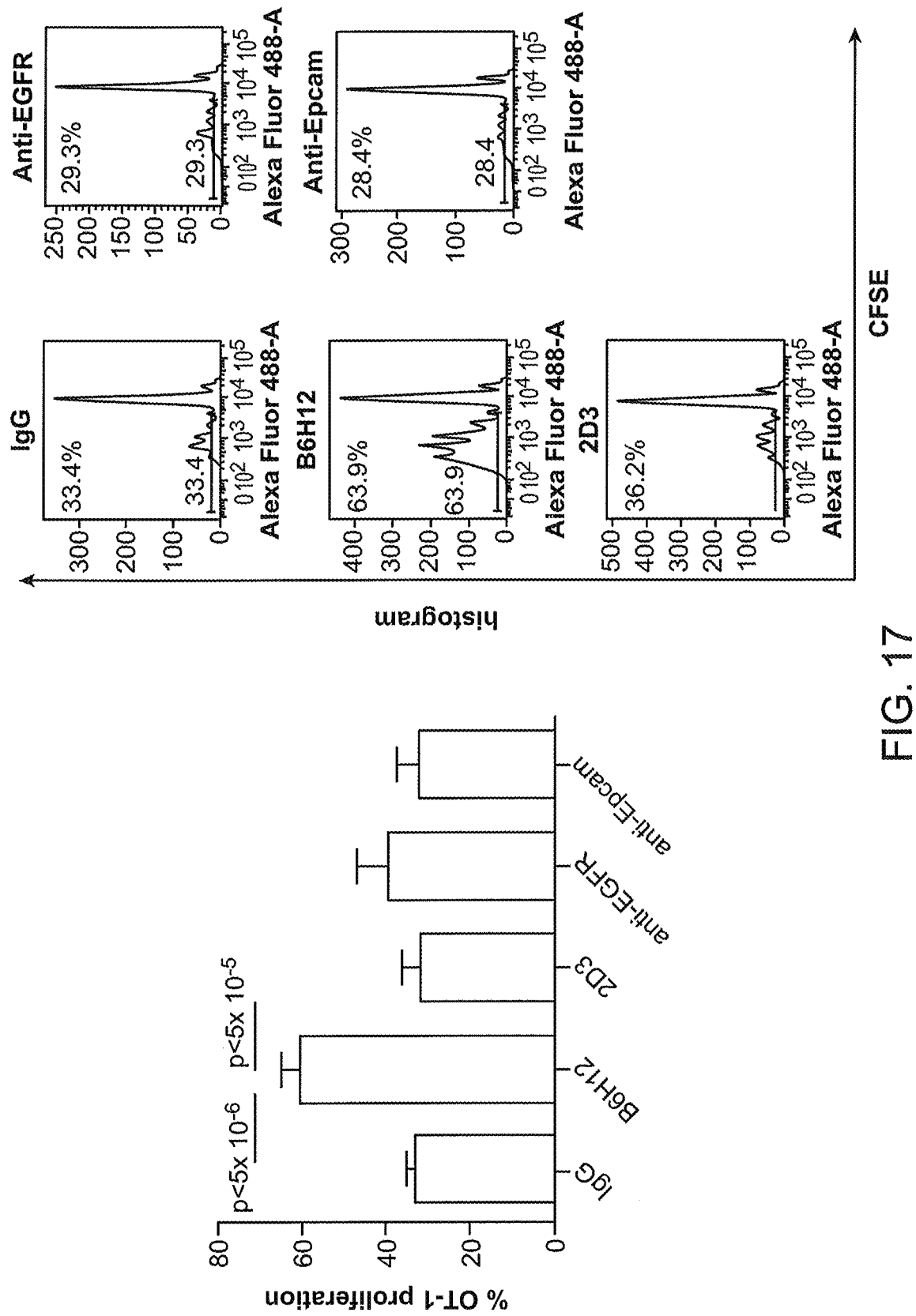
FIG. 17. Phagocytosis of cancer cells by macrophages via anti-CD47, but not anti-EGFR or anti-Epcam, leads to increased priming of CD8+ T cells. RFP+ macrophages were co-cultured with DLD1-cOVA-GFP cancer cells in the presence of IgG, anti-CD47 B6H12 (blocking), or anti-CD47 2D3 (non-blocking), anti-EGFR, and anti-Epcam mAbs. The following day, CD8+ T cells were magnetically enriched from OT-I transgenic mice and labeled with CFSE (0.5 µM). Analysis was performed on day 3 and % proliferating cells determined. This result demonstrates that anti-CD47-mediated phagocytosis provides a unique route for priming a cytotoxic T cell response.

In order to assess the functional effects of anti-CD47 B6H12-mediated phagocytosis on CD4$^+$ regulatory T cells, we crossed OT-II transgenic mice with Foxp3-GFP reporter mice to generate double transgenic mice (FIG. 12). These mice express 25% Foxp3-GFP$^+$ cells within the CD4$^+$ CD25$^+$ population and exhibit Va2 restriction (FIG. 12A). In addition, CD4$^+$ Foxp3-GFP$^+$ T cells are responsive to ovalbumin peptide 323-339 and can be induced to differentiate in the context of TGF-6 and all-trans-retinoic acid (FIG. 12B). RFP$^+$ macrophages were co-cultured with DLD1-cOVA-GFP cancer cells in the presence of IgG, blocking anti-CD47 B6H12, or nonblocking anti-CD47 2D3 mAbs. The following day, CD4$^+$ T cells were magnetically enriched from OT-II/Foxp3-GFP$^+$ double transgenic mice and added to the cultures. After 4 days, the percentage of regulatory T cell was quantified by the percentage of CD4$^+$ Foxp3-GFP$^+$ cells (FIG. 4). A reduction in Foxp3$^+$ regulatory T cells was observed after CD4$^+$ T cells encountered macrophages phagocytosing cancer cells in the presence of anti-CD47 B6H12 mAb.

Following Anti-CD47 Mediated Phagocytosis of Cancer Cells, Macrophages Prime OT-1 (CD8$^+$) T Cells In Vivo.

To evaluate the effects of anti-CD47 B6H12-mediated phagocytosis on CD8$^+$ T cell activation in vivo, OT-I (CD8$^+$) T cells (CD45.2) were CFSE-labeled and adoptively transferred to CD45.1 recipient mice (FIG. 5A). The next day, RFP$^+$ macrophages were cocultured with DLD1-cOVA-GFP tumor cells in the presence of IgG or anti-CD47 B6H12. Macrophages were isolated by magnetic enrichment and phagocytosis verified by FACS analysis prior to subcutaneous transfer into the footpad. After 4 days, the popliteal lymph node was analyzed for the percentage of proliferating cells (CFSE low) within the CD45.2+ gate. There was an increase in proliferating OT-I T cells in mice receiving macrophages that had phagocytosed cancer by an anti-CD47-dependent mechanism (FIG. 5B).

Macrophages Prime an Anti-Tumor CD8 T Cells Response In Vivo Following Anti-CD47-Mediated Phagocytosis of Cancer Cells.

We next evaluated the functional effects of OT-I (CD8$^+$) T cells activation following anti-CD47-mediated phagocytosis of cancer cells by macrophages. To assess the efficiency of CD8$^+$ T cell killing of ovalbumin peptide-displaying targets, CD8$^+$ T cells were isolated from OT-I transgenic mice and intravenously transferred to recipient mice (FIG. 6A). RFP$^+$ macrophages were co-cultured with DLD1-cOVA-GFP cancer cells in vitro in the presence of anti-CD47 B6H12 or IgG mAbs. After a 2-hour incubation, macrophages were isolated and injected into the footpad. After four days, mice were challenged with target cells (CD45.1 splenocytes) to assess cytotoxic activity. CFSE-high splenocytes were pulsed with 1 uM OVA class I-restricted peptide (SIINFEKL, SEQ ID NO:1) to make them targets for OT-I cytotoxic T cells, and then mixed in a 1:1 ratio with non-peptide-pulsed CFSE-low cells before intravenous transfer. Analysis of draining lymph nodes 16 hours later showed increased cell killing of peptide-pulsed CFSE-$^{high}$ lymphocytes in mice receiving macrophages phagocytosing cancer cells with anti-CD47 B6H12 mAb (FIG. 6A).

Next, the ability of CD8$^+$ effector T cells to prime an antitumor immune response was evaluated. CD8+ T cells from OT-I mice were transferred into recipient animals (FIG. 6B). Macrophages were co-cultured with DLD1-cOVA-GFP cancer cells in vitro in the presence of anti-CD47 B6H12 or IgG mAbs, and then the macrophages were transferred into the footpad on days 1 and 10. Animals were challenged with EG.7 (ovalbumin expressing EL4) cancer cells on day 14, and tumor growth was monitored over time. Mice receiving macrophages phagocytosing cancer cells with anti-CD47 B6H12 mAbs demonstrated protection from tumor challenge (FIG. 6B).

The present invention is based on an examination of the role of anti-CD47-enabled phagocytosis on antigen presentation of tumor peptides to T cells of the adaptive immune system. It is demonstrated that CD47 serves as an 'invisibility cloak' for both innate and adaptive immunity. Treatment with blocking anti-CD47 mAbs led to adaptive T cell immune responses, thereby providing an additional mechanism of action for anti-CD47 antibodies.

Ovalbumin-specific OT-I (CD8+) and OTII (CD4+) T cell clones were used to follow the outcomes of antigen presentation by macrophages after anti-CD47-mediated phagocytosis of cancer cells engineered to express cytoplasmic ovalbumin. Using in vitro and in vivo assays, we show that antigens are effectively presented to CD8+ T cells. On the contrary, the level of proliferative response of OT-II CD4+ T cells to loaded macrophages was diminished compared to baseline levels. The baseline level of OT-I CD8+ proliferation and OT-II CD4+ proliferation was 20% (FIG. 2 and FIG. 3), likely due to ovalbumin released from cancer cells that become endocytosed or pinocytosed by macrophages, and are then processed for presentation to both MHC I and MHC II pathways.

Together, these results demonstrate that anti-CD47-mediated phagocytosis of cancer cells results in negative signals presented to CD4+ T cells and positive signals presented to CD8+ T cells. In addition, the CD4+ T cell response was characterized by reduced regulatory T cells. This may be attributed to either decreased proliferation of regulatory T cells in response to peptide or due to less efficient regulatory T cell differentiation. The in vivo priming of an anti-tumor T cell response by macrophages following anti-CD47-mediated phagocytosis of cancer protects mice from tumor challenge. Anti-CD47 mAbs represent a novel therapeutic strategy for overcoming the regulatory T cell contribution to immune evasion by cancer and initiating an effective anti-tumor cytotoxic T cell response.

In this system macrophages are more efficient than dendritic cells at phagocytosing cancer in response to anti-CD47 antibody. This may be due to the higher levels of SIRP☐ found on macrophages compared to DC or due more efficient phagocytosis of whole cells by macrophages. Because dendritic cells subsets have been reported to vary in their levels of SIRP☐ expression, it is possible that other dendritic cell subsets may more efficiently phagocytose cancer in response to anti-CD47 antibody in vivo. However, we show that both macrophages and dendritic cells prime a CD8+ T cell response following anti-CD47 mediated phagocytosis. The detailed roles of tissue-specific DCs and macrophages warrant further investigation both in mouse and human systems.

These findings demonstrate a novel role of macrophages in presenting tumor antigens to CD8+ T cells and mediating antitumor immunity. The involvement of both the innate and adaptive immune systems in the mechanism of action of anti-CD47 antibody has clinical implications. Successful therapeutic use of the antibody might not require that tumor associated macrophages engulf every cancer cell, and may involve CD8+ T cells killing cancer cells not accessible by macrophages. In designing clinical trial protocols for testing anti-CD47 therapy in patients, immune monitoring of T cells will be important for understanding clinical response to treatment and clinical outcomes. Finally, the role of T cells should be taken into careful consideration when designing combination therapies involving anti-CD47 antibodies. Anti-CD47 mAbs find use clinically as a cancer vaccination in combination with adoptive T cell therapy or T cell activating antibodies to enhance the adaptive immune response against tumor antigens.

We conclude that anti-CD47 mediated phagocytosis of cancer not only functions in directly clearing cancer cells, but it also initiates an anti-tumor T cell response to eliminate tumors. Patients receiving anti-CD47 therapy can benefit from both the innate and adaptive immune responses against the cancer.

Materials and Methods

Mice. Mice were bred and maintained at the Stanford University Research Animal Facility in accordance with the Administrative Panel on Laboratory Animal Care, including C57BL/Ka (CD45.2), C57BL/Ka (CD45.1), and C57BL/Ka Rosa26-mRFP1 mice. All of the animals were housed in sterile microinsulators and given water and rodent chow ad libitum. OT-I TCR transgenic mice, OT-II TCR transgenic mice, and Foxp3-GFP mice were purchased from the Jackson laboratory.

Molecular Biology. Cytoplasmic ovalbumin was cloned from pCl-neo-cOVA (plasmid 25097, AddGene) and shuttled into the lentiviral vector pCDH-EF1-MCS-T2A-copGFP vector (System Biosciences) using EcoRl and BamHl restriction sites. Lentiviral production and concentration was accomplished using standard protocols.

Generation of macrophages and dendritic cells. Whole bone marrow cells were isolated from C57BL/Ka (CD45.2)

or C57BL/Ka Rosa26-mRFP1 mice. Macrophages were generated by incubation of whole bone marrow in MCSF 10 ng/mL for 7 days and harvesting of the adherent fraction. Dendritic cells were generated in GM-CSF (1000 U/mL), washed and exchanged with fresh media on days 2 and 4. Non-adherent cells were replated on day 6, and harvested on day 7.

In Vitro Phagocytosis Assay. For in vitro phagocytosis assay, $2 \times 10^4$ macrophages or dendritic cells per well were plated in a 96-well ultra low adherent plate, along with $2 \times 10^4$ cancer cells (DLD1-cOVA-GFP) in serum-free RPMI media. The indicated antibodies (10 μg/mL) were added and incubated for 4 h at 37°. Macrophages were repeatedly washed twice and analyzed using a BD LSR Fortessa Analyzer. The % phagocytosis was calculated as the % GFP+ cells within RFP+ macrophages or F4/80+ macrophages. For in vivo transfer assays, $5 \times 10^5$ macrophages and cancer cells were co-cultured in the presence of control IgG1 or anti-CD47 B6H12 mAb (10 μg/mL) and incubated for 2 hours. Macrophages were then separated from the cultures during anti-Mac-1 magnetic beads (Miltenyi Biotec).

Antigen presentation assay. For in vitro antigen presentation assays, $10^4$ macrophages were cocultured with equal numbers of DLD1-cOVA-GFP cancer cells overnight in serum-free RPMI media. The following day, equal volume of RPMI+20% FCS was added to the cultures. Peripheral lymph nodes were harvested from OT-I or OT-II TCR transgenic mice and labeled with 0.5 mM CFSE (Molecular Probes). T cells were isolated using biotinylated anti-CD8 or anti-CD4 antibodies, followed by enrichment with anti-biotin magnetic beads (Miltenyi Biotec). $5 \times 10^4$ T cells were added to the cultures and analyzed at day 3 (for OT-I T cells) or day 4 (for OT-II T cells). For in vivo antigen presentation assays, $2 \times 10^6$ CFSE-labeled OT-I T cells (CD45.2) were adoptively transferred iv into recipient mice (CD45.1). Macrophages were isolated from co-culture with cancer cells as previously described and injected into the footpad of mice. Popliteal lymph nodes were analyzed on day 4 for CFSE dilution within CD45.2+ cells.

Antibody Preparation, Flow Cytometry Analysis, and Cell Sorting. Mouse anti-human anti-CD47 mAb B6H12 (IgG1) was obtained from Bio-X-Cell. Mouse-anti-human anti-CD47 mAb 2D3 (IgG1) and mouse IgG1 antibodies were obtained from ebiosciences. For verification of binding of anti-CD47 B6H12 and 2D3 to DLD1-cOVA-GFP cancer, cells were labeled with a saturating concentration of a 1:1 anti-CD47 antibody, followed by PE conjugated donkey-anti-mouse IgG (H&L) (Ebiosciences). Data were acquired using a BD LSR Fortessa Analyzer and analyzed using FlowJo software.

In vivo cell killing assay. In brief, splenocytes from C57BL/Ka (CD45.1) mice were labeled with 10 □M CFSE (CFSE-high) and 1 □M CFSE (CFSE-low). CFSE-high splenocytes were then pulsed in a 6-well plate with 1 □M SIINFEKL (SEQ ID NO:1) peptide for 1 hour. Cells were then mixed in a 1:1 ratio with non-peptide-pulsed CFSE-low cells before iv transfer. To account for variation in the CFSE high/low ratio in the absence of peptide-specific lysis, control mice received CFSE-high splenocytes not pulsed with SIINFEKL (SEQ ID NO:1) peptide before mixing in a 1:1 ratio with CFSE-low splenocytes and transfer to mice. Draining lymph nodes were analyzed 16 hours later. Percent cytotoxicity was calculated as $(1 - \% \text{CFSE}^{high} / \% \text{CFSE}^{low})$ normalized to the ratio in control mice receiving splenocytes not pulsed with SIINFEKL (SEQ ID NO:1) peptide.

Tumor challenge. $1 \times 10^6$ CD8-enriched OT-I T cells were adoptively transferred iv into recipient C57BL/Ka mice. Macrophages from syngeneic C57BL/Ka mice were co-cultured with DLD1-cOVA-GFP cancer as previously described, and then isolated by magnetic enrichment and injected into the footpad of mice. The tumor cell line E.G7 (EL.4 cells expressing the chicken OVA cDNA) were used for tumor challenge of mice (ATCC). $1 \times 10^5$ E.G7 cells were injected s.c. into the right hindlimb of the mice in a 1:1 ratio with regular matrigel. Tumor size was measured every day by using fine calipers and volume calculated based on length*width*height*$\pi$/6.

Luminex assay. Macrophages were co-cultured with equal numbers of DLD1-cOVAGFP cancer cells overnight in serum-free RPMI media. The following day, supernatants were harvested and submitted to the Stanford Human Immune Monitoring Core for cytokine analysis by mouse 26-plex luminex assay.

Example 2

Generation of Human Antigen Presenting Cells

Human Macrophages. PBMC or leukophoresis monocytes (fresh or frozen) (from CD14+ cells by positive or negative selection, plastic adherence, Percoll, flow sorting, counterflow centrifugal elutriation). Differentiate in media alone or recombinant human M-CSF to generate monocyte-derived macrophage, as described by Harding et al, Choosing and Preparing Antigen-Presenting Cells. Current Protocols in Immunology. 2010, 16.1.1-16.1.30.

Human Dendritic Cells. Culture monocytes in vitro in the presence of GM-CSF+IL-4 to generate Dermal-like CD1a+ cDC, as described by (Merad et al, Annu Rev Immunol 2013. 31:563-604).

Human Dendritic Cells. Culture CD34+ hematopoietic progenitors in the presence of Flt3L and thrombopoietin to generate pDC, BDCA3+ cDC, BDCA1+ cDC as described by (Merad et al, Annu Rev Immunol 2013. 31:563-604). Alternatively culture in the presence of GM-CSF+TNFalpha to generate LC-like cells and dermal DC-like cells; or in the presence of GM-CSF+TNFalpha+TGF-beta to generate LC-like cells. Monocytes can be cultured with GM-CSF+IL-4+ TGF-beta to generate LC-like cells.

Human Dendritic Cells. PBMC or leukocyte-enriched leukophoresis packet (fresh, not frozen) can be enriched with anti-CD1c bead enrichment kit (commercial) after B cell depletion to provide CD1c+(BDCA1+) DC as described by Harding et al, Choosing and Preparing Antigen-Presenting Cells. Current Protocols in Immunology. 2010, 16.1.1-16.1.30. Alternatively anti-CD141 bead enrichment kit (commercial) to generate CD141+ (BDCA3+) DC; or culture with GM-CSF+IL-4 (can be further activated by TNF-alpha or TLR ligand) to generate monocyte-derived DC.

PBMC can be adhered to plastic for one hour, then cultured in GM-CSF+IL-4 for 5 days (can be further matured in IL-1b, IL-6, TNF-alpha, PGE2) as described by O'Neill et al. Current Protocols in Immunology, Differentiation of Peripheral Blood Monocytes into Dendritic Cells, 2005, 22F4.1-22F4.9.

What is claimed is:

1. A method of inducing a CD8+ T cell immune response to a target cell selected from a pathogen or pathogen-infected mammalian cell, the method comprising:
 (a) contacting in vitro;
  (i) a phagocytic antigen presenting cell (phAPC) population comprising one or both of mammalian macrophages and dendritic cells,
  (ii) the pathogen or pathogen-infected mammalian target cell,
  (iii) in the presence of an effective dose of an anti-CD47 agent that blocks the interaction between CD47 and SIRPα, selected from: an antibody that binds to CD47, an antibody that binds to SIRPα, a soluble SIRPα-binding CD47 fragment, and a soluble CD47-binding SIRPα fragment; to generate a loaded phAPC population; and
 (b) contacting a CD8+ T cell population with the loaded phAPC population;
 wherein the CD8+ T cell population generates a response specific to the pathogen or pathogen-infected mammalian target cell.

2. The method of claim 1, wherein the target cell is a pathogen-infected cell.

3. The method of claim 1, wherein the target cell is a pathogen.

4. The method of claim 1, wherein the CD8+ T cell population is selectively induced to respond to the target cell.

5. The method of claim 4, wherein the CD8+ T cell population is a human T cell population.

* * * * *